US008655440B2

(12) United States Patent
Adachi et al.

(10) Patent No.: US 8,655,440 B2
(45) Date of Patent: *Feb. 18, 2014

(54) SYSTEM AND METHOD OF SPEECH SOUND INTELLIGIBILITY ASSESSMENT, AND PROGRAM THEREOF

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 405 days.

This patent is subject to a terminal disclaimer.

(21) Appl. No.: 13/037,479

(22) Filed: Mar. 1, 2011

(65) Prior Publication Data

US 2011/0152708 A1    Jun. 23, 2011

Related U.S. Application Data

(63) Continuation of application No. PCT/JP2010/004358, filed on Jul. 2, 2010.

(30) Foreign Application Priority Data

Jul. 3, 2009   (JP) .................................. 2009-159105

(51) Int. Cl.
    *A61B 5/04*    (2006.01)
(52) U.S. Cl.
    USPC .............................. 600/544; 381/60; 704/200
(58) Field of Classification Search
    USPC ........ 600/544, 545; 607/57; 381/60; 704/200
    See application file for complete search history.

(56) References Cited

U.S. PATENT DOCUMENTS

| 6,602,202 B2 * | 8/2003 | John et al. ..................... 600/559 |
| 2001/0049480 A1 | 12/2001 | John et al. |
| 2006/0114222 A1 | 6/2006 | Araki et al. |
| 2009/0259277 A1 * | 10/2009 | Cornejo Cruz et al. ......... 607/57 |

FOREIGN PATENT DOCUMENTS

| JP | 06-114038 A | 4/1994 |
| JP | 07-039540 A | 2/1995 |
| JP | 09-038069 A | 2/1997 |
| JP | 2002-346213 A | 12/2002 |
| JP | 2003-319497 A | 11/2003 |
| WO | 2006/003901 A1 | 1/2006 |

OTHER PUBLICATIONS

Co-pending U.S. Appl. No. 12/959,513, filed Dec. 3, 2010.

(Continued)

*Primary Examiner* — Navin Natnithithadha
*Assistant Examiner* — Etsub Berhanu
(74) *Attorney, Agent, or Firm* — Renner, Otto, Boisselle & Sklar, LLP

(57) ABSTRACT

A speech sound intelligibility assessment system includes: a biological signal measurement section for measuring an electroencephalogram signal of a user; a presented-speech sound control section for determining a speech sound to be presented by referring to a speech sound database retaining a plurality of monosyllabic speech sounds; an audio output section for presenting the speech sound determined by the presented-speech sound control section as an audio; a characteristic component detection section for utilizing the electroencephalogram signal of the user measured by the biological signal measurement section to determine presence or absence of a characteristic component of an event-related potential at 800 ms±100 ms from a point of presenting the audio; and a speech sound intelligibility assessment section for, based on a result of determination by the characteristic component detection section, determining whether the user has aurally comprehended the speech sound or not.

10 Claims, 17 Drawing Sheets

(56) References Cited

OTHER PUBLICATIONS

International Search Report for corresponding International Application No. PCT/JP2010/004358 mailed Aug. 10, 2010.

Kazuoki Kodera, Shindan to Chiryosha, "Hochoki Fittingu No Kangaekata" (or "Concept of Hearing Aid Fitting"), 1999, p. 172 and an English translation.

Kaga et al., "Event-Related Potential (ERP) Manual-mailing concerning P300", Shinohara Shuppan Shinsha, 1995 and a partial English translation.

Kanzaki et al., "Hochoki Q&A—Yoriyoi Fittingu Notameni", (or "Hearing aids Q&A—For better Fitting"), Kanehara & Co., Ltd., 2001, p. 79 and an English translation.

"Shin Seirishinrigaku" (or "New Physiopsychology"), supervised by Yo Miyata, vol. 2, pp. 14-15 and a partial English translation, dated Sep. 20, 1997.

\* cited by examiner

FIG.1

| | PROCEDURE A | | PROCEDURE B | PROCEDURE C | PROCEDURE D |
|---|---|---|---|---|---|
| | ↻ [　] | NA → SPACE | [　] | な | ASSESSMENT |

| CONDITION | NA-/MA-ROW<br>RA-/YA-ROW  } 0dB or<br>KA-/TA-ROW  } -50dB | | | NA 50%<br>MA 50% | |
|---|---|---|---|---|---|
| USER<br>STATE | HEAR AUDIO<br>AND THINK OF<br>A HIRAGANA | | SPACE KEY<br>("NEXT" BUTTON) | NA: EXPECTED<br>MA: WHAT? | 5: ABSOLUTELY MATCHING<br>4: PROBABLY MATCHING<br>3: NOT SURE<br>2: PROBABLY MISMATCHING<br>1: ABSOLUTELY MISMATCHING |

FIG.4
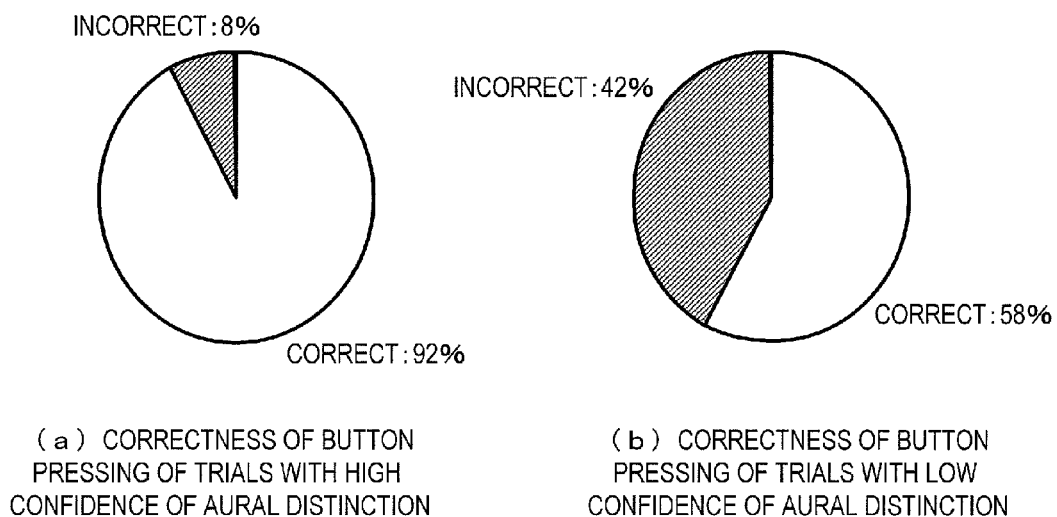
(a) CORRECTNESS OF BUTTON
PRESSING OF TRIALS WITH HIGH
CONFIDENCE OF AURAL DISTINCTION
(b) CORRECTNESS OF BUTTON
PRESSING OF TRIALS WITH LOW
CONFIDENCE OF AURAL DISTINCTION
FIG.5　　The 10-20 system
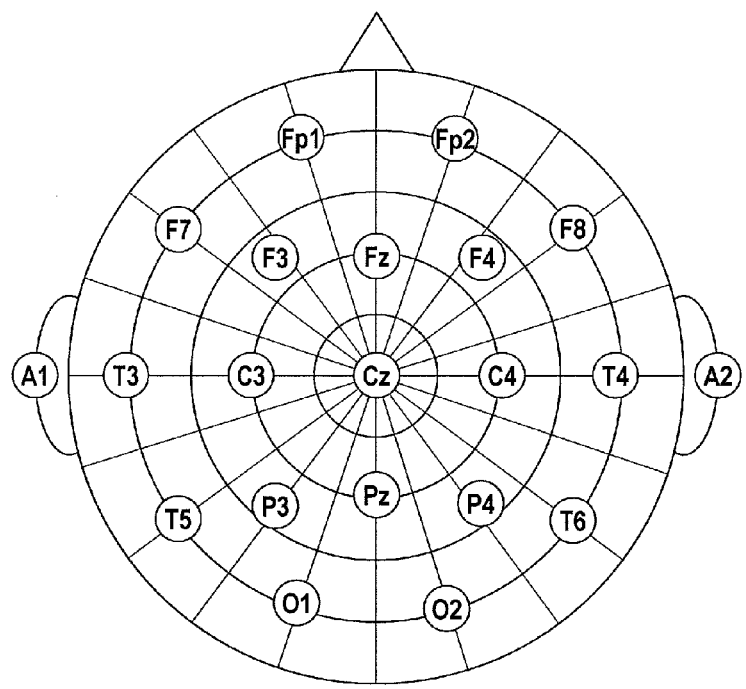

FIG.10
| | | CONFIDENCE OF AURAL DISTINCTION | SPEECH DISCRIMINABILITY |
|---|---|---|---|
| POSITIVE COMPONENT @Pz | NO | HIGH | ○ (CLEAR) |
| | YES | LOW | △ (UNCLEAR) |
FIG.11
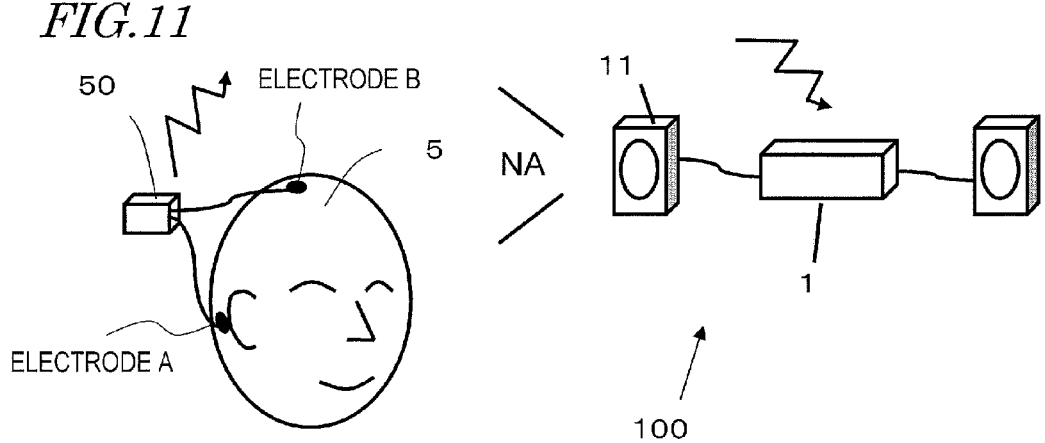
FIG.12
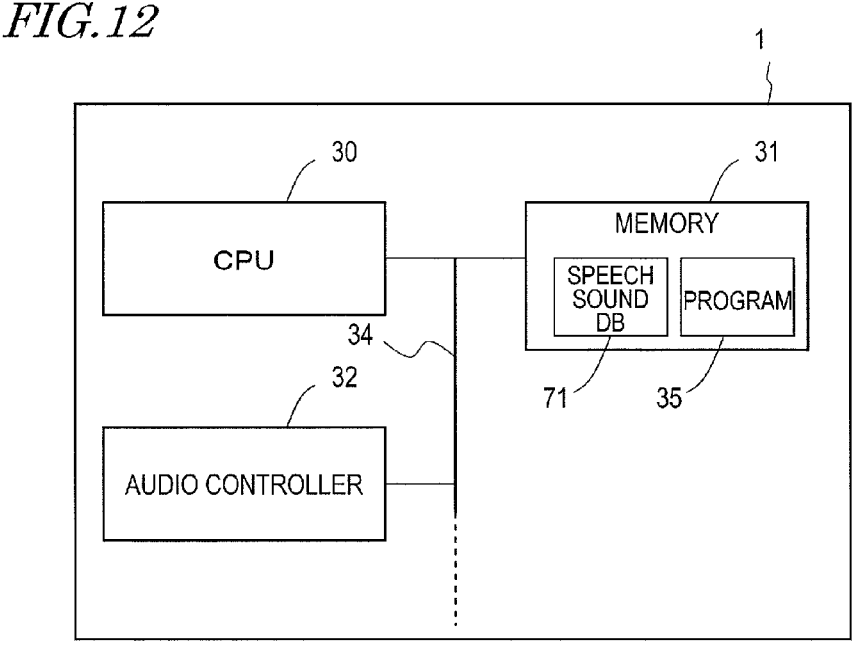

*FIG.14*

| SPEECH SOUND | AUDIO FILE | CON-SONANT LABEL | GROUP | | |
|---|---|---|---|---|---|
| | | | ROUGH CATEGORY | MEDIUM CATEGORY | FINE CATEGORY |
| a | a.wav | − | 0 | 0 | 0 |
| i | i.wav | − | 0 | 0 | 0 |
| u | u.wav | − | 0 | 0 | 0 |
| e | e.wav | − | 0 | 0 | 0 |
| o | o.wav | − | 0 | 0 | 0 |
| ka | ka.wav | k | 1 | 2 | 0 |
| sa | sa.wav | s | 1 | 1 | 0 |
| ta | ta.wav | t | 1 | 2 | 0 |
| na | na.wav | n | 2 | 2 | 1 |
| ha | ha.wav | h | 1 | 2 | 0 |
| ma | ma.wav | m | 2 | 2 | 1 |
| ya | ya.wav | y | 2 | 1 | 0 |
| ra | ra.wav | r | 2 | 1 | 0 |
| wa | wa.wav | w | 2 | 1 | 0 |
| ga | ga.wav | g | 2 | 2 | 2 |
| za | za.wav | z | 2 | 2 | 2 |
| da | da.wav | d | 2 | 2 | 2 |
| ba | ba.wav | b | 2 | 2 | 2 |
| ... | ... | ... | ... | ... | ... |

| SPEECH SOUND | ASSESS-MENT |
|---|---|
| a | ○ |
| i | ○ |
| u | ○ |
| e | ○ |
| o | ○ |
| ka | ○ |
| sa | ○ |
| ta | ○ |
| na | △ |
| ha | ○ |
| ma | △ |
| ya | ○ |
| ra | △ |
| wa | ○ |
| ga | ○ |
| za | ○ |
| da | △ |
| ba | ○ |
| ... | ... |

(a) SPEECH SOUND-BY-SPEECH SOUND ASSESSMENT

| CONSONANT LABEL | ASSESS-MENT |
|---|---|
| k | ○ |
| s | ○ |
| t | ○ |
| n | △ |
| h | ○ |
| m | △ |
| y | △ |
| r | △ |
| w | ○ |
| g | △ |
| z | ○ |
| d | △ |
| b | ○ |
| ... | ... |

(b) CONSONANT-BY-CONSONANT ASSESSMENT

| GROUP | | | ASSESS-MENT |
|---|---|---|---|
| ROUGH CATEGORY | MEDIUM CATEGORY | FINE CATEGORY | |
| 0 | 0 | 0 | ○ |
| 1 | 1 | 0 | ○ |
| 1 | 2 | 0 | △ |
| 2 | 1 | 1 | ○ |
| 2 | 1 | 2 | ○ |
| 2 | 2 | 1 | △ |
| 2 | 2 | 2 | △ |
| ... | ... | ... | ... |

(c) GROUP-BY-GROUP ASSESSMENT

*FIG.17*

| WORD | ASSESS-MENT |
|---|---|
| sit | ○ |
| meet | ○ |
| get | ○ |
| cat | ○ |
| come | ○ |
| hot | ○ |
| law | ○ |
| book | ○ |
| blue | △ |
| urge | ○ |
| star | △ |
| page | ○ |
| sky | △ |
| join | ○ |
| now | ○ |
| home | ○ |
| here | △ |
| care | ○ |
| ... | ... |

| PHONETIC SYMBOL | ASSESS-MENT |
|---|---|
| i | ○ |
| e | ○ |
| æ | ○ |
| ə | △ |
| ɜ | ○ |
| ei | △ |
| ai | △ |
| au | △ |
| p | ○ |
| b | △ |
| t | ○ |
| d | △ |
| k | ○ |
| ... | ... |

| GROUP | | | ASSESS-MENT |
|---|---|---|---|
| ROUGH CATEGORY | MEDIUM CATEGORY | FINE CATEGORY | |
| 0 | 0 | 0 | ○ |
| 1 | 1 | 0 | ○ |
| 1 | 2 | 0 | △ |
| 2 | 1 | 1 | ○ |
| 2 | 1 | 2 | ○ |
| 2 | 2 | 1 | △ |
| 2 | 2 | 2 | △ |
| ... | ... | ... | ... |

(a) WORD-BY-WORD ASSESSMENT (b) PHONETIC SYMBOL-BY-PHONETIC SYMBOL ASSESSMENT (c) GROUP-BY-GROUP ASSESSMENT

FIG.20

| SPEECH SOUND | AUDIO FILE | CON-SONANT LABEL | GROUP | | |
|---|---|---|---|---|---|
| | | | ROUGH CATEGORY | MEDIUM CATEGORY | FINE CATEGORY |
| a | a.wav | – | 0 | 0 | 0 |
| i | i.wav | – | 0 | 0 | 0 |
| u | u.wav | – | 0 | 0 | 0 |
| e | e.wav | – | 0 | 0 | 0 |
| o | o.wav | – | 0 | 0 | 0 |
| ka | ka.wav | k | 1 | 2 | 0 |
| sa | sa.wav | s | 1 | 1 | 0 |
| ta | ta.wav | t | 1 | 2 | 0 |
| na | na.wav | n | 2 | 2 | 1 |
| ha | ha.wav | h | 1 | 2 | 0 |
| ma | ma.wav | m | 2 | 2 | 1 |
| ya | ya.wav | y | 2 | 1 | 0 |
| ra | ra.wav | r | 2 | 1 | 0 |
| wa | wa.wav | w | 2 | 1 | 0 |
| ga | ga.wav | g | 2 | 2 | 2 |
| za | za.wav | z | 2 | 2 | 2 |
| da | da.wav | d | 2 | 2 | 2 |
| ba | ba.wav | b | 2 | 2 | 2 |
| ... | ... | ... | ... | ... | ... |

FIG.21

| FITTING METHOD A | | FITTING METHOD B | | FITTING METHOD C | |
|---|---|---|---|---|---|
| SPEECH SOUND | DISCRIMINA-BILITY | SPEECH SOUND | DISCRIMINA-BILITY | SPEECH SOUND | DISCRIMINA-BILITY |
| a | ○ | a | ○ | a | ○ |
| i | ○ | i | ○ | i | ○ |
| u | ○ | u | ○ | u | ○ |
| e | ○ | e | ○ | e | ○ |
| o | ○ | o | ○ | o | ○ |
| ka | ○ | ka | △ | ka | ○ |
| sa | ○ | sa | ○ | sa | ○ |
| ta | ○ | ta | △ | ta | ○ |
| na | △ | na | △ | na | △ |
| ha | ○ | ha | ○ | ha | ○ |
| ma | ○ | ma | △ | ma | △ |
| ya | ○ | ya | ○ | ya | ○ |
| ra | △ | ra | △ | ra | △ |
| wa | ○ | wa | ○ | wa | ○ |
| ga | ○ | ga | △ | ga | △ |
| za | ○ | za | ○ | za | ○ |
| da | △ | da | △ | da | △ |
| ba | ○ | ba | ○ | ba | ○ |
| ... | ... | ... | ... | ... | ... |

FIG.22

| | PROBABILITY OF CLEAR SPEECH SOUNDS | ASSESSMENT RESULT |
|---|---|---|
| FITTING METHOD A | 85 % | ◎ |
| FITTING METHOD B | 60 % | × |
| FITTING METHOD C | 75 % | △ |

SYSTEM AND METHOD OF SPEECH SOUND INTELLIGIBILITY ASSESSMENT, AND PROGRAM THEREOF

This is a continuation of International Application No. PCT/JP2010/004358, with an international filing date of Jul. 2, 2010, which claims priority of Japanese Patent Application No. 2009-159105, filed on Jul. 3, 2009, the contents of which are hereby incorporated by reference.

BACKGROUND OF THE INVENTION

1. Field of the Invention

The present invention relates to a technique for evaluating whether a speech sound has been aurally comprehended or not. More specifically, the present invention relates to a speech sound intelligibility assessment system for evaluating the degree of "fitting" of a hearing aid or the like to provide a sound of appropriate loudness for each individual user by adjusting the amount of amplification of sounds with respect to each frequency. "Intelligibility" is sometimes referred to as "discrimination score".

2. Description of the Related Art

In recent years, people suffering from presbycusis are increasing in number due to the aging society. Moreover, due to increased opportunities for listening to loud music for long hours as well as other influences, there is an increasing number of people suffering from hypacusia associated with acoustic traumas.

Moreover, due to the downsizing and improved performance of hearing aids, users feel less of a psychological barrier against wearing hearing aids. Thus, there is an increasing number of users who use hearing aids in order to improve conversational listening comprehension in daily life.

A hearing aid is a device for compensating for the deteriorated hearing of a user by amplifying sounds of frequencies which are difficult for the user to hear. The amount of sound amplification which a user desires in a hearing aid varies depending on the level of deterioration in the hearing of the user. Therefore, before beginning use of a hearing aid, "fitting" is required for adjusting the amount of sound amplification in accordance with the hearing of each user.

Fitting is performed in such a manner that the output sound pressure level of a hearing aid is at an MCL (most comfortable level: a sound pressure level that is comfortable to a user) for each frequency. Problems may occur if fitting is not appropriately done. For example, if the amount of amplification is insufficient, sounds may not be sufficiently heard; or if the amplification is excessive, the user may feel that it is too loud.

Fitting is generally performed based on each user's audiogram. An "audiogram" is a result of evaluating how a pure tone is "heard": for example, a diagram in which, for each of a number of sounds of different frequencies (e.g., 250 Hz, 500 Hz, 1000 Hz, 2000 Hz, 4000 Hz), the smallest sound pressure level (decibel value) that the user can hear is plotted against frequency.

In order to perform fitting, it is necessary to generate an audiogram for each user first. Then, the generated audiogram is subjected to a fitting method, which is a mathematical function for estimating an MCL for each user.

Currently, however, there is no one established fitting method that can determine an optimum amount of sound amplification with respect to any and every user for improving the conversational listening comprehension intelligibility from his or her audiogram alone. Possible reasons are, for example: an audiogram is not in one-to-one correspondence with a conversational listening comprehension ability; a person suffering from hypacusia has a narrow range of sound pressure that is felt to him or her as an appropriate loudness; and a plurality of fitting methods are diversely present.

Therefore, in order to evaluate the degree of fitting, a speech sound intelligibility assessment is needed. A "speech sound intelligibility assessment" is an assessment as to whether a speech sound has actually been aurally comprehend or not, and is an assessment of listening comprehension ability as to whether a monosyllabic speech sound has been aurally comprehend or not. A monosyllabic speech sound means either a single vowel or a combination of a consonant and a vowel (e.g., "あ (a)"/"だ (da)"/"し (shi)"). Since the purpose of wearing a hearing aid is aural distinction in conversations, assessment results of speech sound intelligibility are regarded as important.

Conventionally, speech sound intelligibility assessment has been performed through the following procedure. First, by using the 57S list (50 monosyllables) or the 67S list (20 monosyllables) proposed by the Japan Audiological Society, a user is allowed to hear a monosyllabic audio via oral presentation or CD reproduction. Next, through oral explanation, writing, or other methods, the user is asked to answer which speech sound he or she has aurally comprehended the presented speech sound to be. Then, an evaluator matches the answers against the list in order to calculate a correctness rate.

However, in the aforementioned assessment method, the user is required to make answers via oral explanation or writing, and the evaluator needs to determine the correctness of the user's answers through manual labor. Thus, this test presents a large burden, and is time-consuming, on the part of the user and the evaluator.

Therefore, for example, Japanese Laid-Open Patent Publication No. 9-038069 discloses a speech sound intelligibility assessment method which, in order to reduce the burden of the evaluator, employs a personal computer (PC) to automatically perform correctness determination. Specifically, Japanese Laid-Open Patent Publication No. 9-038069 proposes a method in which monosyllabic audios are presented to a user by using a PC; the user is asked to answer by using a mouse or via pen-touch technique; the answers are received as inputs to the PC; and correctness determinations as to the presented audios and answer inputs are automatically made. Since answer inputs are received by using a mouse or via pen-touch technique, there is no need for the evaluator to analyze and distinguish the user's answers (which are given by oral explanation or writing), whereby the trouble of the evaluator is greatly reduced.

Moreover, for example, Japanese Laid-Open Patent Publication No. 6-114038 discloses a speech sound intelligibility assessment method in which, after audio presentation, possible choices of speech sounds are presented in the form of text characters, thus reducing the user's burden of making answer inputs. In Japanese Laid-Open Patent Publication No. 6-114038, choices are limited to only a small number so that the relevant speech sound can be found among the small number of characters, whereby the user's trouble of finding the character is reduced. Also in Japanese Laid-Open Patent Publication No. 6-114038, a PC is used to receive answer inputs, thus reducing the evaluator's burden.

However, in the speech sound intelligibility assessment methods described in Japanese Laid-Open Patent Publication Nos. 9-038069 and 6-114038, the user needs to make answer inputs. Therefore, an answer-inputting operation still exists, thus presenting a burden on the user. In particular, it is presumably not easy for people suffering from hypacusia or elderly people who are unaccustomed to working on a PC to make answer inputs by using a mouse or a touch pen. There has also been a possibility that the wrong monosyllable matrix may be inadvertently selected through a manipulation mistake, in which case the speech sound intelligibility may not be correctly evaluated.

SUMMARY OF THE INVENTION

An objective of the present invention is to realize a speech sound intelligibility assessment system in which the user does not need to perform cumbersome answer-inputting.

A speech sound intelligibility assessment system according to the present invention includes: a biological signal measurement section for measuring an electroencephalogram signal of a user; a presented-speech sound control section for determining a speech sound to be presented by referring to a speech sound database retaining a plurality of monosyllabic speech sounds; an audio output section for presenting the speech sound determined by the presented-speech sound control section as an audio; a characteristic component detection section for utilizing the electroencephalogram signal of the user measured by the biological signal measurement section to determine presence or absence of a characteristic component of an event-related potential at 800 ms±100 ms from a point of presenting the audio; and a speech sound intelligibility assessment section for, based on a result of determination by the characteristic component detection section, determining whether the user has aurally comprehended the speech sound or not.

The event-related potential may be acquired by utilizing an electrode position Pz according to the International 10-20 system, and the characteristic component detection section may determine that a characteristic component exists in the event-related potential when a component equal to or greater than a predetermined value is present in the event-related potential, and in this case, if the characteristic component detection section determines that the characteristic component does not exist in the event-related potential, the speech sound intelligibility assessment section may determine that the user has aurally comprehended the speech sound, and if the characteristic component detection section determines that the characteristic component exists in the event-related potential, the speech sound intelligibility assessment section may determine that the user has not aurally comprehended the speech sound.

The event-related potential may be acquired by utilizing an electrode position Cz according to the International 10-20 system, and the characteristic component detection section may determine that a characteristic component exists in the event-related potential when a component equal to or less than a predetermined value is present in the event-related potential, and in this case, if the characteristic component detection section determines that the characteristic component does not exist in the event-related potential, the speech sound intelligibility assessment section may determine that the user has aurally comprehended the speech sound, and if the characteristic component detection section determines that the characteristic component exists in the event-related potential, the speech sound intelligibility assessment section may determine that the user has not aurally comprehended the speech sound.

In the speech sound database, an audio, consonant information, and a group concerning probability of confusion may be associated with each of a plurality of speech sounds.

The speech sound intelligibility assessment section may evaluate a speech sound intelligibility for each speech sound, each consonant, or each group concerning probability of confusion.

The speech sound database may retain a plurality of audio sets whose frequency gain is adjusted by a plurality of fitting methods; and the speech sound intelligibility assessment system may further comprise a fitting method switching section for selecting one of the plurality of fitting methods by regularly or randomly switching between the audio sets retained in the speech sound database.

When the audio output section presents as an audio a speech sound from within an audio set selected by the fitting method switching section, among the plurality of fitting methods, the speech sound intelligibility assessment section may make a comparison as to the respective results of determination as to whether the speech sound has been aurally comprehended or not, and determine the fitting method having a highest probability that the speech sound has been aurally comprehended to be suitable to the user.

Another speech sound intelligibility assessment system according to includes: a presented-speech sound control section for determining a speech sound to be presented by referring to a speech sound database retaining a plurality of monosyllabic speech sounds; an audio output section for presenting the speech sound determined by the presented-speech sound control section as an audio; a characteristic component detection section for utilizing an electroencephalogram signal of a user measured by a biological signal measurement section for measuring the electroencephalogram signal of the user to determine presence or absence of a characteristic component of an event-related potential at 800 ms±100 ms from a point of presenting the audio; and a speech sound intelligibility assessment section for, based on a result of determination by the characteristic component detection section, determining whether the user has aurally comprehended the speech sound or not.

A speech sound intelligibility assessment method according to the present invention may comprise the steps of: measuring an electroencephalogram signal of a user; determining a speech sound to be presented by referring to a speech sound database retaining a plurality of monosyllabic speech sounds; presenting the determined speech sound as an audio; from the measured electroencephalogram signal of the user, determining presence or absence of a characteristic component of an event-related potential at 800 ms±100 ms from a point of presenting the audio; and determining whether the user has aurally comprehended the speech sound or not based on a result of determination.

A computer program according to the present invention is a computer program, stored on a non-transitory computer-readable medium, to be executed by a computer for evaluating speech sound intelligibility, wherein the computer program causes the computer to execute the steps of: receiving a measured electroencephalogram signal of a user; determining a speech sound to be presented by referring to a speech sound database retaining a plurality of monosyllabic speech sounds; presenting the determined speech sound as an audio; from the measured electroencephalogram signal of the user, determining presence or absence of a characteristic component of an event-related potential at 800 ms±100 ms from a point of presenting the audio; and determining whether the user has aurally comprehended the speech sound or not based on a result of determination.

According to the present invention, based on the presence or absence of a characteristic component of an electroencephalogram at the central portion of the head of a user after an audio is presented, it is possible to quantitatively and automatically evaluate whether the user has aurally comprehended the presented speech sound. This makes it unnecessary for the user to make cumbersome answer inputs, whereby an assessment of listening comprehension results is realized which presents little burden on both an evaluator and the user.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 1 is a diagram describing the experimental procedure of a behavioral experiment in outline.

Portions (a) and (b) of FIG. 4 are diagrams showing degrees of confidence in aural distinction of audios by participants, as categorized based on results of button pressing, and correctness/incorrectness probabilities of button pressing.

FIG. 5 is a diagram showing electrode positions according to the International 10-20 system.

Figure 6:
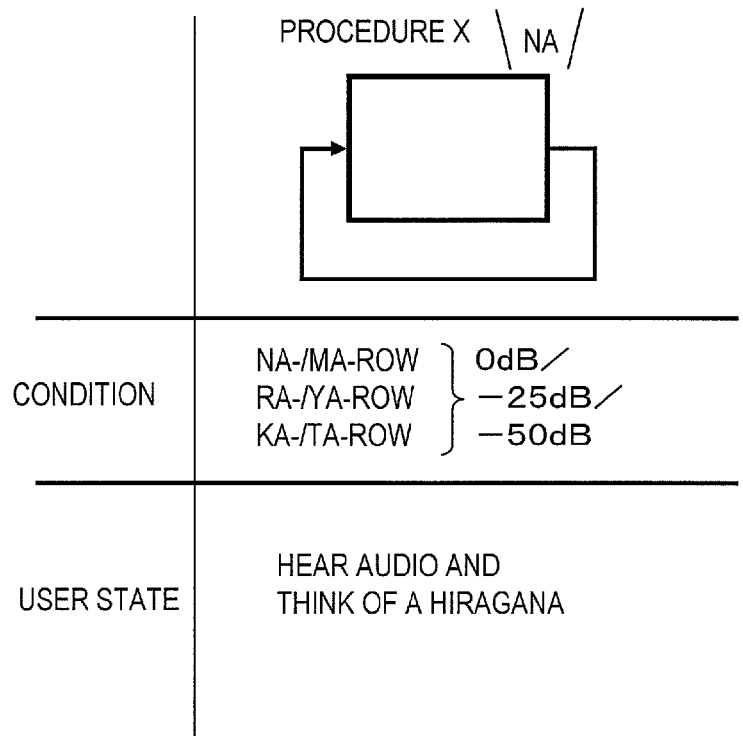

FIG. 6 is a diagram showing the experimental procedure of an electroencephalogram measurement experiment in outline.

Figure 7:
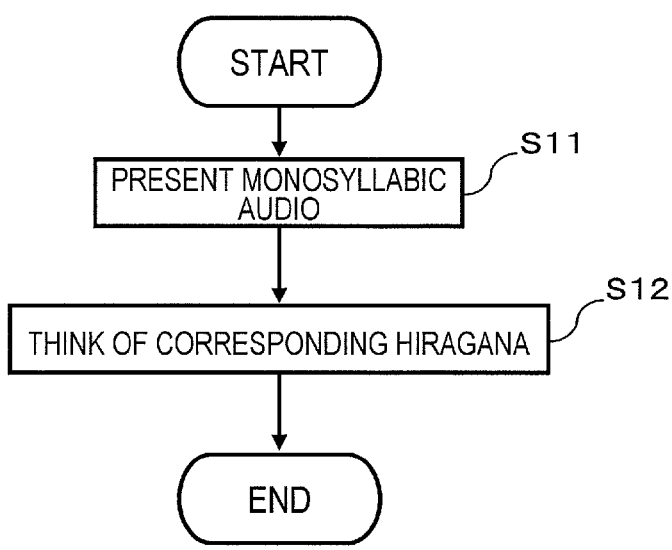

FIG. 7 is a flowchart showing a procedure corresponding to one trial.

Figure 8:
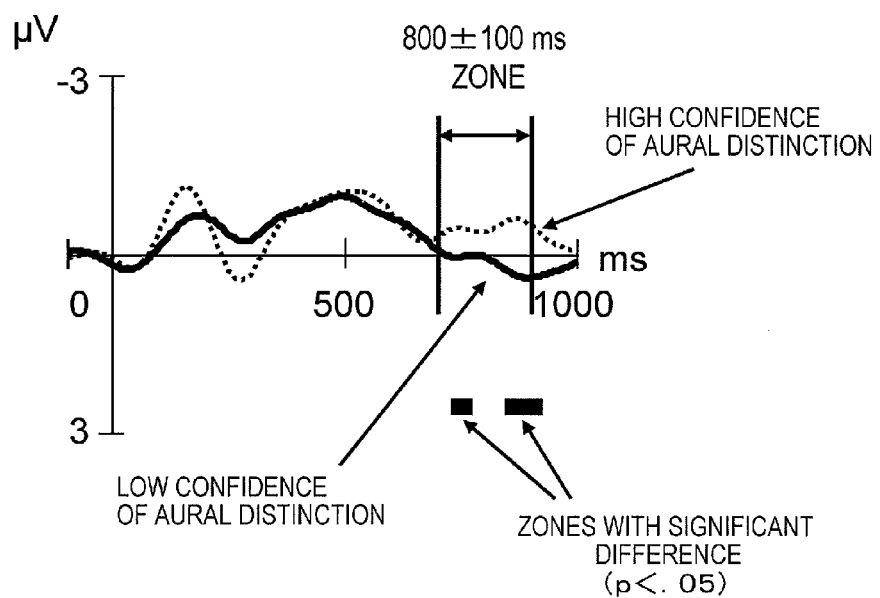

FIG. 8 is a waveform diagram showing event-related potentials at Pz, based on audio presentation as a starting point, where total arithmetic means are taken based on confidence of aural distinction.

Figure 9:
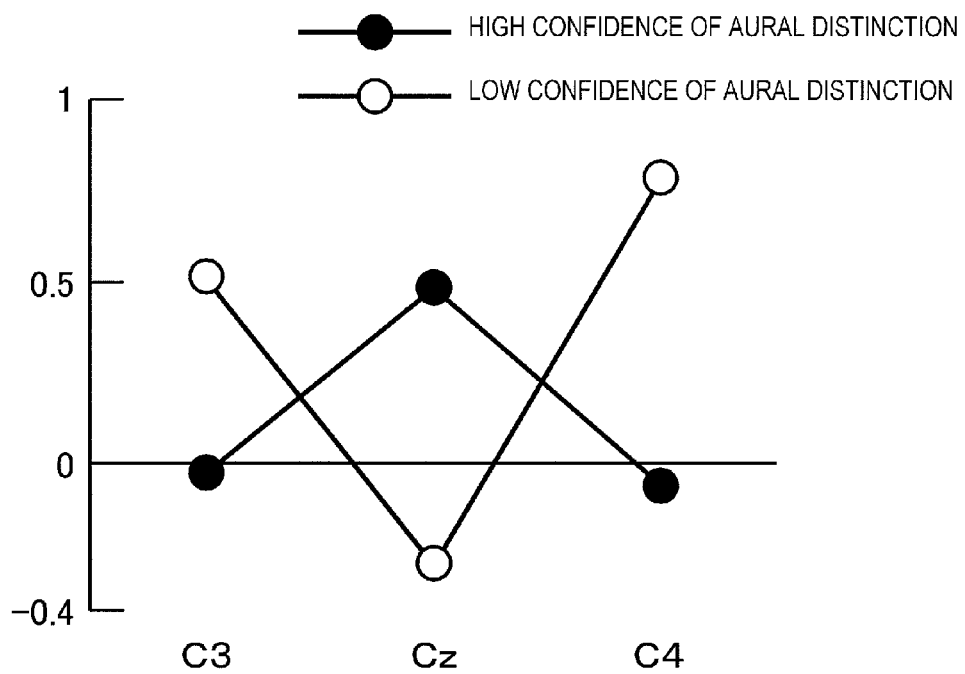

FIG. 9 is a diagram showing zone average potentials of event-related potentials from 700 ms to 900 ms at electrode positions C3, Cz, and C4, based on the point of audio presentation as a starting point, with respect to different degrees of confidence of aural distinction.

FIG. 10 is a diagram, compiled by the inventors, showing correspondence between presence or absence of a positive component and confidence of aural distinction and ease of hearing.

FIG. 11 is a diagram showing a construction and an environment of use for a speech sound intelligibility assessment system 100 according to Embodiment 1.

FIG. 12 is a diagram showing the hardware construction of a speech sound intelligibility assessment apparatus 1 according to an embodiment.

Figure 13:
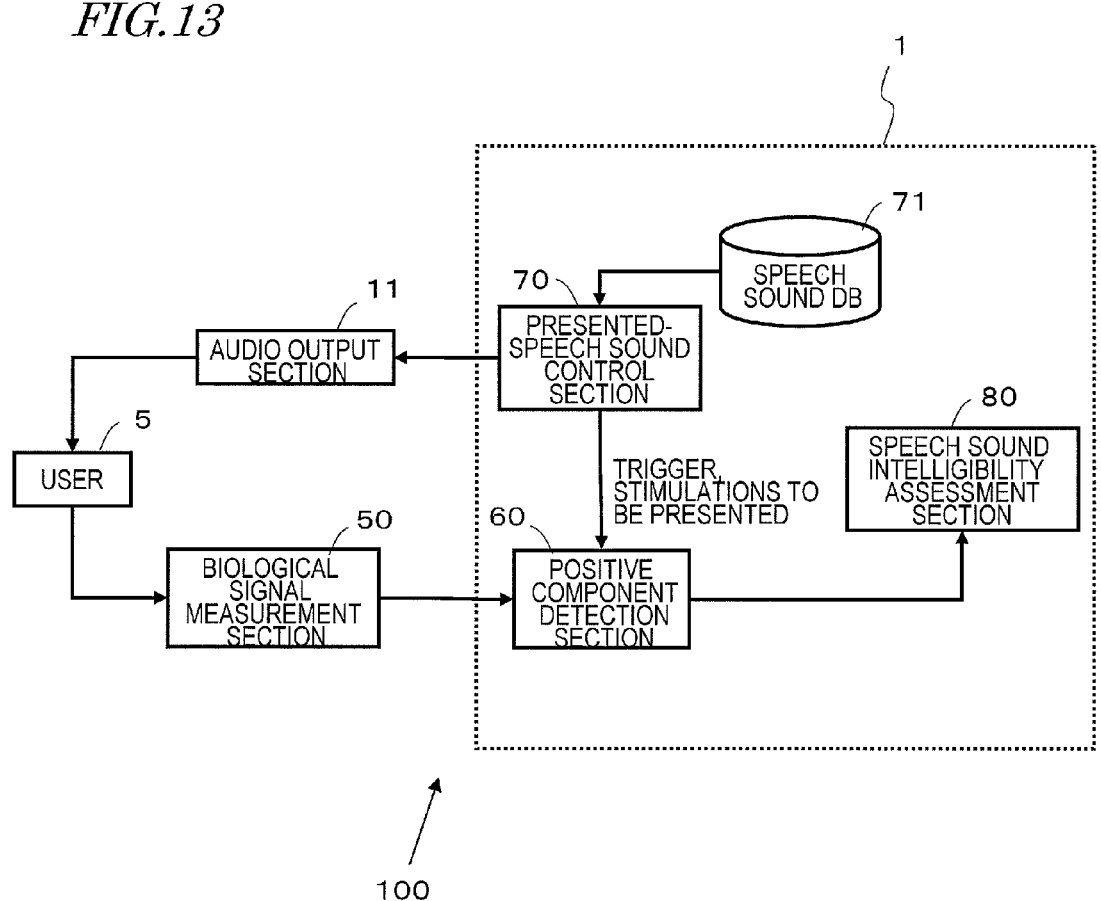

FIG. 13 is a diagram showing a functional block construction of the speech sound intelligibility assessment system 100 according to the embodiment.

FIG. 14 is a diagram showing an example of a speech sound DB 71.

Portions (a) to (c) of FIG. 15 are diagrams showing exemplary results of speech sound intelligibility assessment.

Figure 16:
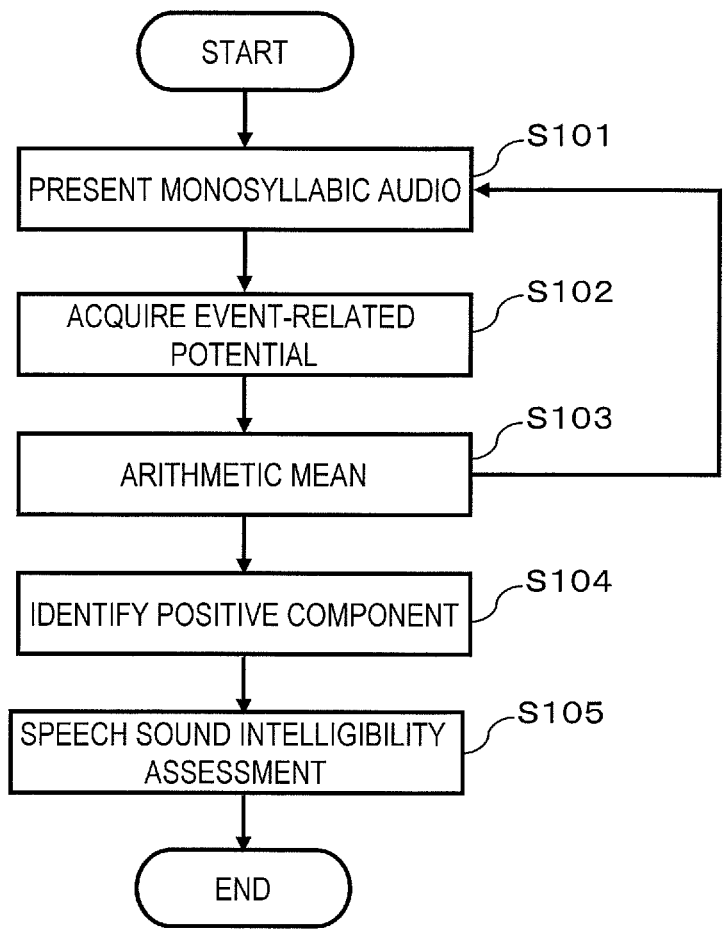

FIG. 16 is a flowchart showing a procedure of processing performed by the speech sound intelligibility assessment system 100.

Portions (a) to (c) of FIG. 17 are diagrams showing exemplary results of speech sound intelligibility assessment in the case of English.

Figure 18:
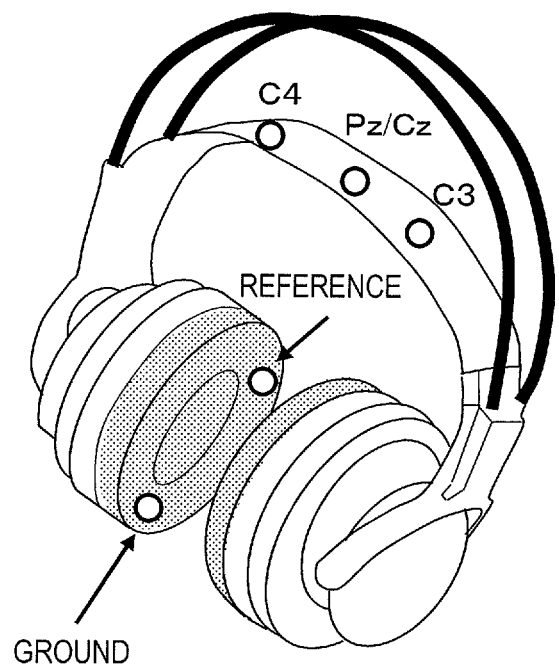

FIG. 18 is a diagram showing the exterior appearance of a pair of headphones corresponding to an audio output section 11.

Figure 19:
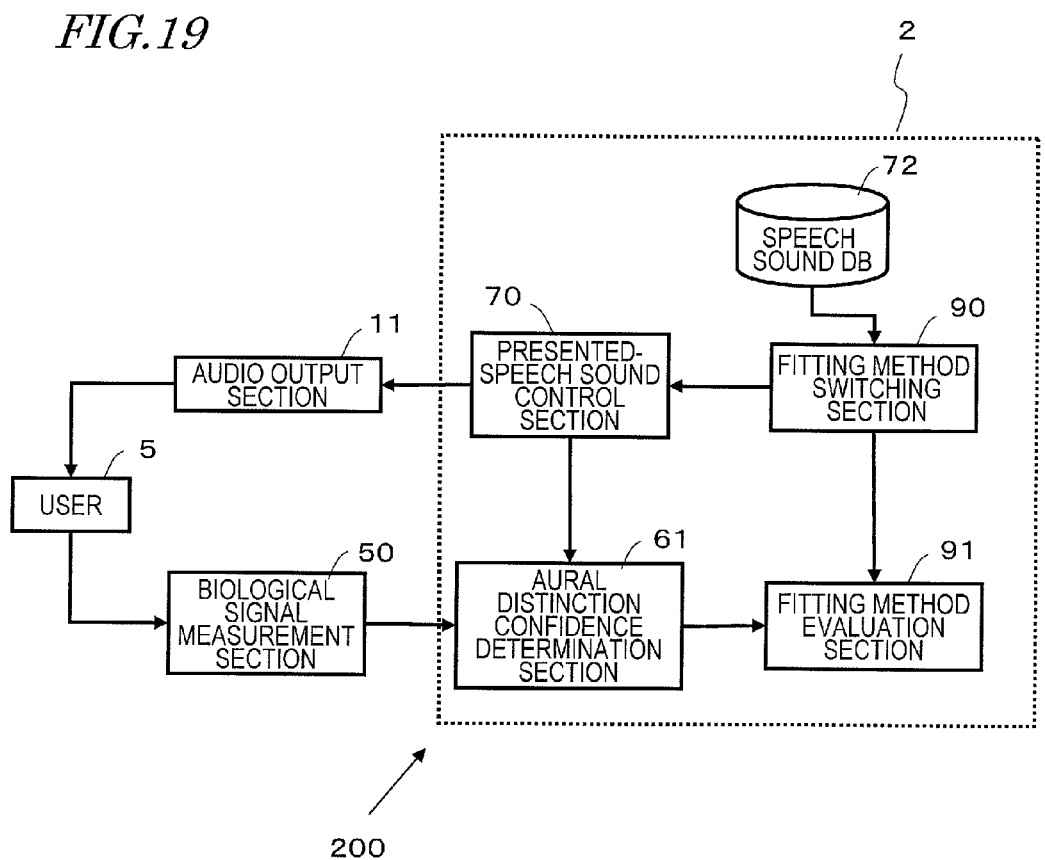

FIG. 19 is a diagram showing a functional block construction of a speech sound intelligibility assessment system 200 according to Embodiment 2.

FIG. 20 is a diagram showing an example of a speech sound DB 72 according to Embodiment 2.

FIG. 21 is a diagram showing examples of results of speech sound intelligibility assessment for different speech sounds according to fitting methods A to C.

FIG. 22 is a diagram showing exemplary assessment results of fitting methods.

Figure 23:
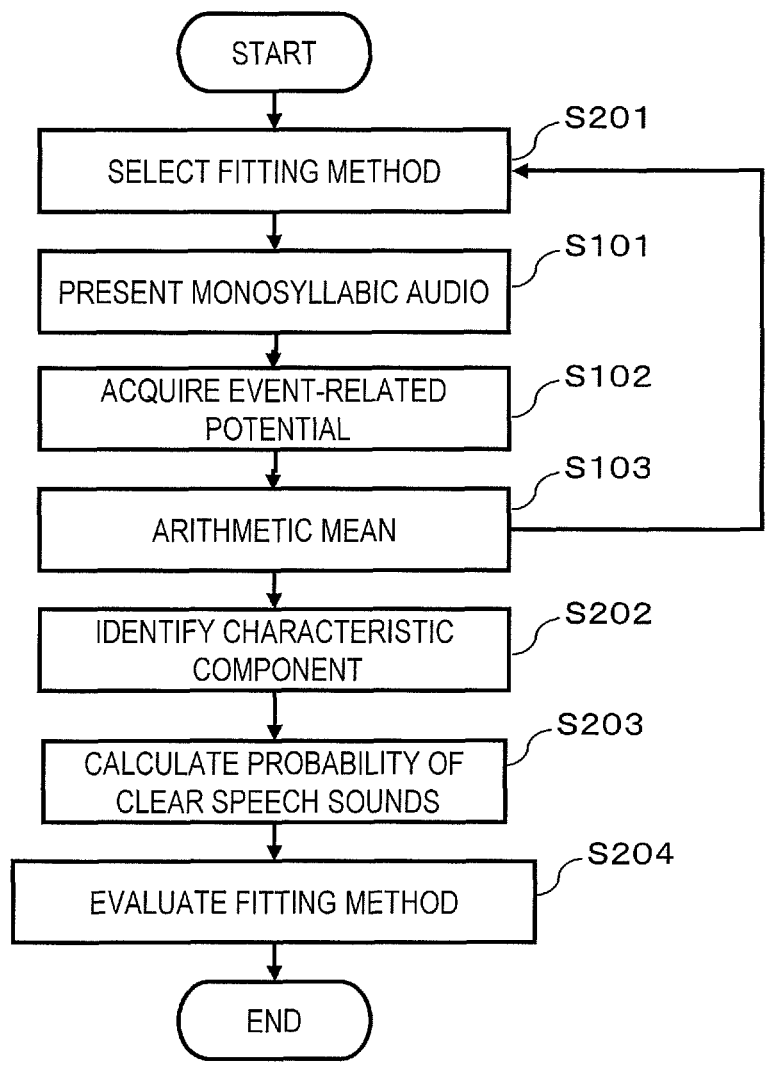

FIG. 23 is a flowchart showing a processing procedure by the speech sound intelligibility system 200 according to an embodiment.

DETAILED DESCRIPTION OF PREFERRED EMBODIMENTS

Hereinafter, with reference to the attached drawings, embodiments of the speech sound intelligibility assessment system according to the present invention will be described.

A speech sound intelligibility assessment system according to the present invention is used for evaluating a speech sound intelligibility by utilizing an electroencephalogram. More specifically, the speech sound intelligibility assessment system is used for evaluating aural distinction concerning speech sounds on the premise of presenting a monosyllabic speech sound in the form of an audio and asking the user to aurally distinguish the audio, where an event-related potential of an electroencephalogram signal from a user is utilized as an index, based on the point of audio presentation as a starting point. In the present specification, to "present an audio" means to output an auditory stimulation, e.g., outputting an audio through a loudspeaker. Note that the type of loudspeaker may be arbitrary. It may be a loudspeaker which is placed on the floor or on a stand, or may be the loudspeakers of a pair of headphones.

The inventors have conducted the following two kinds of experiments for realizing a speech sound intelligibility assessment which does not require answer inputs by a user.

First, the inventors conducted a behavioral experiment for examining the relationship between confidence of aural distinction concerning audios and probability of confusion. Specifically, a monosyllabic speech sound(s) were presented in the form of an audio and a character (hiragana), and a user was asked to confirm whether the audio and the character were identical, who used a button to indicate his or her confidence of listening comprehension concerning the audio. This allowed the inventors to recognize the facts that the probability of confusion is as low as 10% or less when the confidence of aural distinction concerning the audio is high, and that the probability of confusion is high when the confidence of aural distinction is low.

Next, the inventors conducted an experiment where, on the premise of presenting a monosyllabic speech sound in the form of an audio and asking a user to think of a speech sound corresponding to the audio, an event-related potential was measured based on the point of audio presentation as a starting point. Then, based on the confidence of aural distinction previously acquired through a behavioral experiment, an arithmetic mean of the event-related potential was taken. It was thus found that, when the confidence of aural distinction for the audio is high, a positive component is induced in the neighborhood of the central portion of the head at a latency from 700 ms to 900 ms in the event-related potential based on an audio stimulation as a starting point, as compared to the case where the confidence of aural distinction for the audio is low.

An "event-related potential" is a portion of an electroencephalogram, referring to a transient potential fluctuation in the brain which occurs in temporal relationship with an external or internal event. Herein, it is meant as a potential fluctuation that is related to a presented audio.

A "latency" indicates an amount of time from a point of presenting an audio stimulation until when a peak of a positive or negative component appears.

From the above recognition and findings, it has been found that a speech sound intelligibility can be evaluated on the basis of a confidence of aural distinction concerning audios, which can be determined from the presence or absence of a positive component in an event-related potential at a latency from 700 ms to 900 ms based on the point of audio presentation as a starting point. Conventionally, a speech sound intelligibility assessment is made based only on whether a user's answer is correct or not. In contrast, the present approach realizes a speech sound intelligibility assessment based on whether the user believes that he or she has aurally distinguished an audio or not, as opposed to whether an audio has actually been correctly aurally distinguished or not.

These will be described in more detail below. Firstly, a behavioral experiment and an electroencephalogram measurement experiment which were conducted by the inventors in order to realize a speech sound intelligibility assessment which does not require answer inputs by a user will be described. Thereafter, as an embodiment, an outline of a speech sound intelligibility assessment apparatus for evaluating aural distinction concerning speech sounds, as well as a construction and operation of a speech sound intelligibility assessment system including the speech sound intelligibility assessment apparatus, will be described.

1. Behavioral Experiment

The inventors conducted a behavioral experiment in order to example the relationship between confidence of aural distinction concerning audios and probability of confusion. Hereinafter, with reference to FIG. 1 to FIG. 3, the experimental setting and experimental results of the behavioral experiment conducted will be described.

Six undergraduate or graduate students with normal hearing participated in the experiment.

FIG. 1 shows the experimental procedure of the behavioral experiment in outline.

Figure 2:
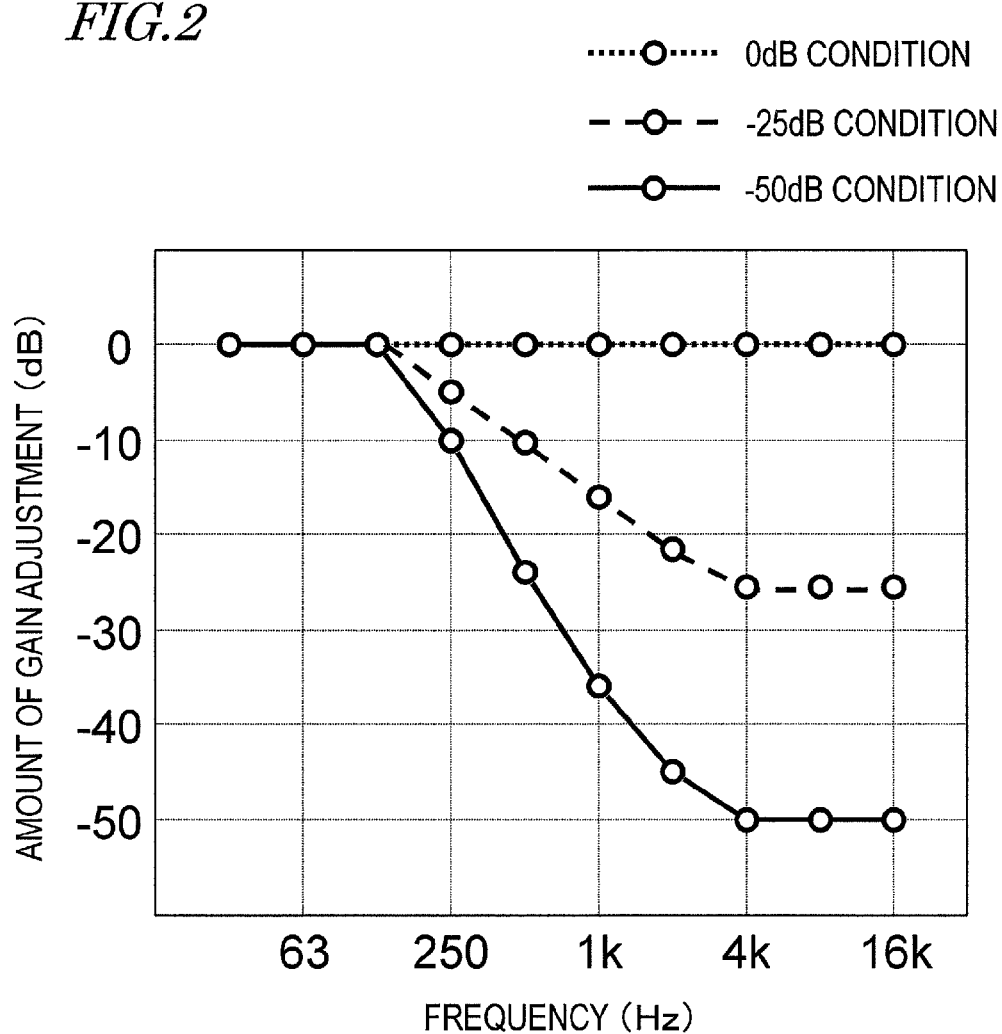
FIG. 2 is a diagram showing amounts of gain adjustment for different frequencies, corresponding to three conditions.

First, a monosyllabic audio was presented in procedure A. With reference to "HOCHOKI FITTINGU NO KANGAEKATA (or "Concept of Hearing Aid Fitting") (Kazuoki KODERA, Shindan To Chiryosha, 1999, p. 172), the stimulation speech sound was selected from among a pair of na- and ma-rows, a pair of ra- and ya-rows, and a pair of ka- and ta-rows, which are known to mutually induce mistakes in listening comprehension. Each experimental participant was instructed to think of a hiragana upon hearing the audio. Audios under the following three conditions were presented, with the frequency gain being modified so that the confidence of aural distinction would be diversified for each audio among participants with normal hearing: (1) (0 dB condition) no frequency gain modification was applied, meant as an audio that is easy to aurally distinguish; (2) (−25 dB condition) the gains for frequencies from 250 Hz to 16 kHz were gradually adjusted to −25 dB (attenuated); and (3) (−50 dB condition) the gains for frequencies from 250 Hz to 16 kHz were gradually adjusted to −50 dB (attenuated). FIG. 2 shows amounts of gain adjustment for different frequencies under conditions (1) to (3). The reason for attenuating the frequency gain for higher frequencies is to reproduce a typical pattern of hypacusia of elderly people. Generally speaking, elderly people suffering from hypacusia are likely to have difficulties in hearing sounds of higher frequencies. By attenuating the frequency gain for higher frequencies, people with normal hearing are allowed to experience a hearing which is similar to the difficult hearing of elderly people suffering from hypacusia.

Next, in procedure B, the experimental participant was asked to press the SPACE key on the keyboard. Procedure B, which concerns a button pressing for being able to proceed to procedure C, was introduced in this experiment to allow the participant to experience the character stimulation of procedure C at his or her own pace. This button is also referred to as the "NEXT" button.

In procedure C, a hiragana character was presented on a display. The character matching the audio presented in procedure A was presented as a matching trial, and a hiragana not matching the audio was presented as a mismatching trial, both with a probability of 0.5. As each mismatching hiragana, a character in a different row from that of the audio was chosen, from within a pair of na- and ma-rows, a pair of ra- and ya-rows, or a pair of ka- and ta-rows (which are generally supposed to induce many mistakes in listening comprehension), while the vowel was not changed. For example, if a hiragana "な (na)" was presented in procedure A, then " な " was to be presented as a matching trial in procedure C, and " ま (ma)" was to be presented as a mismatching trial in procedure C.

Procedure D involves a button pressing (numbers 1 to 5 on the keyboard) for confirming how mismatching the audio presented in procedure A and the character presented in procedure C were to the participant. The participant was supposed to press "5" to express "absolutely matching", "4" to express "probably matching", "3" to express "not sure", "2" to express "probably mismatching", and "1" to express "absolutely mismatching". If 5 or 1 was pressed during this button pressing, it means that, although the participants were diversified between correct and incorrect (as a result of confusion) in procedure C, they were confident in their aural distinction at the point of hearing the audio presented in procedure A. Similarly, if any of 2 to 4 was pressed, it means that the participants were unconfident in their aural distinction of the audio.

In the experiment conducted, procedure A to procedure D described above was repeated 108 times (108 trials).

Figure 3:
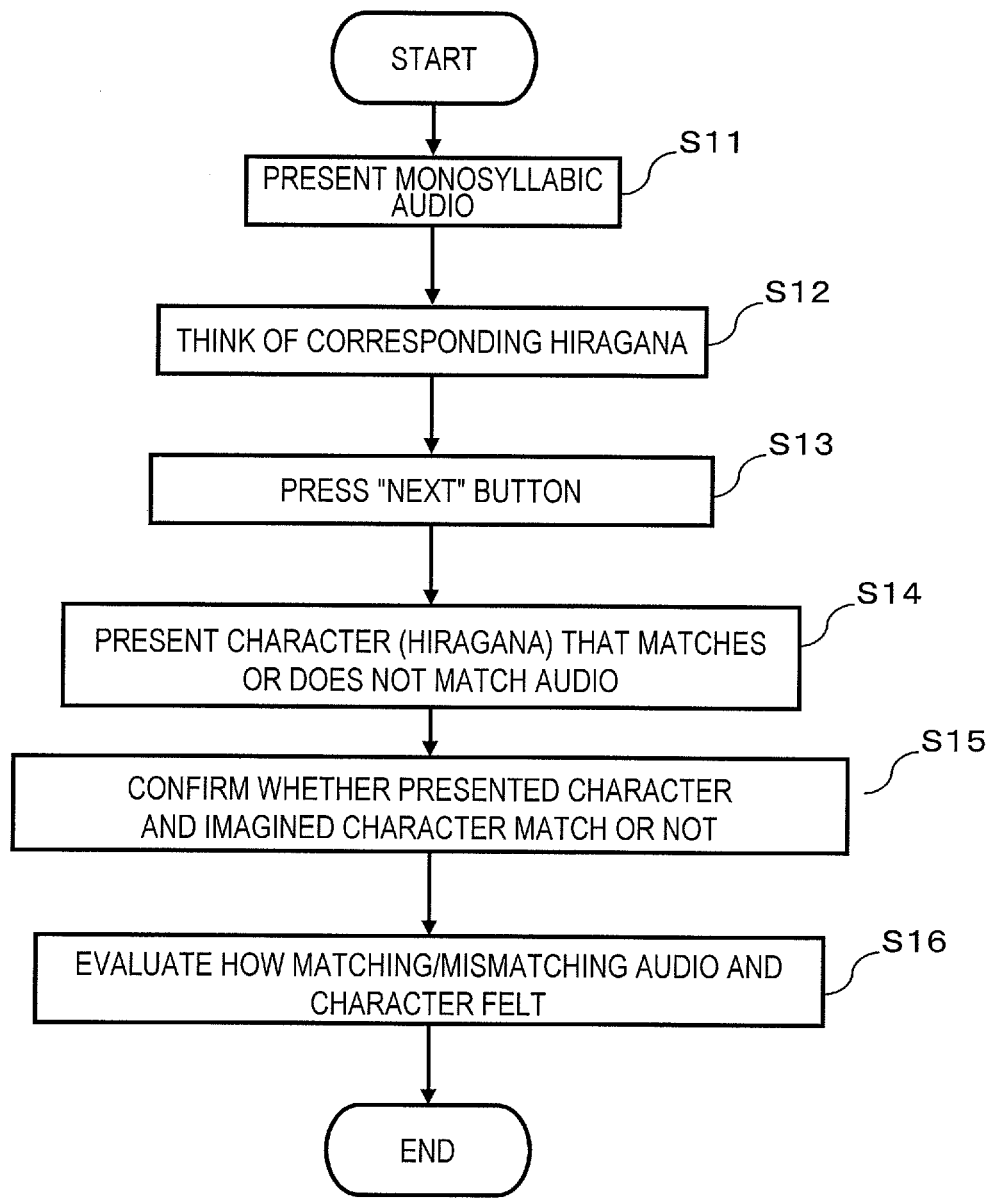
FIG. 3 is a flowchart showing a procedure corresponding to one trial.

FIG. 3 is a flowchart showing a procedure corresponding to one trial. In this flowchart, for ease of explanation, the operation of the apparatus and the operation of the experimental participant are both present.

step S11 is a step of presenting a monosyllabic audio to the experimental participant. The audio was presented under the three conditions of the 0 dB condition, the −25 dB condition, and the −50 dB condition, these conditions being in random order (procedure A).

Step S12 is a step where the participant thinks of a corresponding hiragana upon hearing the monosyllabic audio. Note that a "hiragana" is a character (phonogram) representing a certain pronunciation in the Japanese language. In the case of English or Chinese, as will be described later, the character sequence of a monosyllabic word or a phonetic symbol would correspond to a hiragana.

Step S13 is a step where the participant presses the SPACE key as a "NEXT" button (procedure B).

Step S14 is a step of presenting on a display a hiragana character matching the audio or a hiragana character mismatching the audio, both with a 50% probability as reckoned from step S13 as the starting point (procedure C).

Step S15 is a step of confirming whether the hiragana which the participant thought of at step S12 matches the hiragana presented at step S14.

Step S16 is a step of answering how matching/mismatching they were felt to the participant at step S15, via number keys of 1 to 5 (procedure D).

The experimental results of the behavioral experiment are described below.

FIG. 4 is a diagram showing degrees of confidence in aural distinction of audios by participants, as categorized based on results of button pressing, and correctness/incorrectness probabilities of button pressing. The degrees of confidence of aural distinction were categorized as follows. Any case where 5 (absolutely matching) or 1 (absolutely mismatching) was pressed was defined as case with a "high" confidence of aural distinction. Out of all trials, the probability that the confidence was "high" was 60.4% (522 trials in 864 trials). Any case where 4 (probably matching), 3 (not sure), or 2 (probably mismatching) was pressed was defined as a case with a "low" confidence of aural distinction. Out of all trials, the probability that the confidence was "low" was 39.6% (342 trials in 864 trials). The correctness of button pressing was determined based on matching/mismatching between the audio and the character and the button that was pressed. The cases where 5 (absolutely matching) or 4 (probably matching) was pressed for a matching trial, or 1 (absolutely mismatching) or 2 (probably mismatching) for a mismatching trial were defined as "correct", whereas any other case was defined as "incorrect".

FIG. 4(a) shows correctness/incorrectness results of button pressing in trials with high confidence of aural distinction. It can be seen that the correct button is selected in almost all trials (92%). This indicates that the audio is correctly aurally-distinguished when the confidence of aural distinction is high. Based on these results, it can be said that a high speech sound intelligibility assessment may be made when the confidence of aural distinction is high.

FIG. 4(b) shows correctness/incorrectness results of button pressing in trials with low confidence of aural distinction. It can be seen that there is a high probability that the wrong button was pressed (42%). This indicates that confusion is likely to occur when the confidence of aural distinction is low. Based on these results, it can be said that a low speech sound intelligibility assessment may be made when the confidence of aural distinction is low.

Note that each participant's probability of confusion was significantly high ($p<0.01$) when the confidence of aural distinction was high.

Thus, through the behavioral experiment, a clear possibility has been indicated that speech sound intelligibility assessment can be realized based on a user's confidence of aural distinction concerning audios. Therefore, if confidence of aural distinction can be measured by a method other than button pressing, a speech sound intelligibility assessment not involving any answer inputs can be realized based on that index. Paying attention to the event-related potential of the electroencephalogram, the inventors have conducted an electroencephalogram measurement experiment to examine whether there exists any component that reflects differences in confidence of aural distinction concerning audios. Hereinafter, the electroencephalogram measurement experiment will be described.

2. Electroencephalogram Measurement Experiment

In order to examine a relationship between the confidence of aural distinction concerning audios and the event-related potential after audio presentation, the inventors have conducted an electroencephalogram measurement experiment. Hereinafter, with reference to FIG. 5 to FIG. 9, the experimental setting and experimental results of the electroencephalogram measurement experiment conducted will be described.

The experimental participants were the same six undergraduate or graduate students in the behavioral experiment.

By using electrodes placed at the Fz, Cz, Pz, C3, and C4 positions (International 10-20 system) on the scalp, the inventors have measured and recorded each electroencephalogram on the basis of the right mastoid. A "mastoid" is a protrusion of the cranium at the hind root of an ear. FIG. 5 is a diagram showing the electrode positions according to the International 10-20 system. The sampling frequency was 200 Hz, and the time constant was 1 second. It was subjected to a 1 to 6 Hz digital band-pass filter off-line. As an event-related potential in response to an audio presentation, a waveform from −100 ms to 1000 ms was cut out based on the point of audio presentation as a starting point. An arithmetic mean of the event-related potential was taken based on the confidence of aural distinction with respect to each speech sound and each participant, under each condition (0 dB/−25 dB/−50 dB) in the above-described behavioral experiment.

FIG. 6 shows the experimental procedure of the electroencephalogram measurement experiment in outline.

In procedure X, a monosyllabic audio was presented. Similarly to the behavioral experiment, with reference to "HOCHOKI FITTINGU NO KANGAEKATA (or "Concept of Hearing Aid Fitting") (Kazuoki KODERA, Shindan To Chiryosha, 1999, p. 172), the stimulation speech sound was selected from among a pair of na- and ma-rows, a pair of ra- and ya-rows, and a pair of ka- and ta-rows, which are known to mutually induce mistakes in listening comprehension. Each experimental participant was instructed to think of a hiragana upon hearing the audio. Similarly to the behavioral experiment, audios under the following three conditions were presented, with the frequency gain being modified so that the confidence of aural distinction would be diversified for each audio among participants with normal hearing:

(1) (0 dB condition) no frequency gain modification was applied, meant as an audio that is easy to aurally distinguish;

(2) (−25 dB condition) the gains for frequencies from 250 Hz to 16 kHz were gradually adjusted to −25 dB (attenuated); and (3) (−50 dB condition) the gains for frequencies from 250 Hz to 16 kHz were gradually adjusted to −50 dB (attenuated).

In the experiment conducted, the above procedure X was repeated 108 times (108 trials).

FIG. 7 is a flowchart showing a procedure corresponding to one trial. Any block that has a like counterpart in FIG. 3 will be denoted by a like reference numeral, and the description thereof will be omitted. The difference from FIG. 3 is that step S13 to step S16 are omitted, so that each experimental participant is not required to make any explicit action.

Hereinafter, experimental results of the electroencephalogram measurement experiment will be described.

FIG. 8 shows event-related potentials at Pz, based on audio presentation as a starting point, where total arithmetic means are taken based on confidence of aural distinction. An arithmetic mean of the event-related potential was taken based on the confidence of aural distinction with respect to each speech sound and each participant, under each condition (0 dB/−25 dB/−50 dB) in the above-described behavioral experiment. In FIG. 8, the horizontal axis represents time in units of ms, whereas the vertical axis represents potential in units of μV. As is clear from the scales shown in FIG. 8, the lower direction in the graph corresponding to plus (positive), and the upper direction corresponds to minus (negative). The baseline is set so that an average potential from −100 ms to 0 ms is zero.

In FIG. 8, the solid line represents an arithmetic mean waveform of the event-related potential at the electrode position Pz in the case where the confidence of aural distinction was high in the behavioral experiment, and the broken line represents that of the case where the confidence of aural distinction was low. It can be seen from FIG. 8 that, as compared to the broken line representing a high confidence of aural distinction, a positive component appears at a latency from 700 ms to 900 ms in the solid line representing a low confidence of aural distinction.

A zone average potential from 700 ms to 900 ms of each participant was −0.47 μV in the case of a high confidence of aural distinction, and 0.13 μV in the case of a low confidence. Through a t-test of the zone average potential, it was found that the zone average potential was significantly large in the case of a low confidence of aural distinction (p<0.05).

From these results, the inventors have drawn the conclusion that an event-related potential at a latency from 700 ms to 900 ms based on the point of audio presentation as a starting point reflects confidence of aural distinction, such that the potential can be utilized as an index of confidence of aural distinction. As a result of performing a t-test for every sampling from 0 ms to 1000 ms, the only time slots where a significant difference de to a difference in confidence of aural distinction lasted for 30 ms or more were 730 ms to 770 ms and 840 ms to 915 ms.

FIG. 9 is a diagram showing zone average potentials of event-related potentials from 700 ms to 900 ms at electrode positions C3, Cz, and C4, based on the point of audio presentation as a starting point, with respect to different degrees of confidence of aural distinction. Lines jointed by black circles shown in FIG. 9 represent a zone average potential of the case of a high confidence of aural distinction, and lines jointed by white circles represent the case of a low confidence of aural distinction. As a result of conducting a t-test of the zone average potential with respect to a high confidence and a low confidence for each of the electrode positions C3, Cz, and C4, a significant difference was found for each position (p<0.05).

It can be seen from FIG. 9 that, at the electrode position Cz, the event-related potential is positive in the case of a high confidence of aural distinction, and the event-related potential is negative in the case of a low confidence of aural distinction. Paying attention to the polarity of the event-related potential, it can be seen that the polarity is inverted between the measurements at the electrode position Pz (FIG. 8) and the measurements at the electrode position Cz (FIG. 9). Since the polarity would hardly be reversed between the electrode positions Cz and Pz in a generic P300 component, it is highly possible that the positive component that is induced at the electrode position Pz in the case of a low confidence of aural distinction is a distinct component from the P300 component. According to "SHINSEIRISHINRIGAKU (or "New Physiopsychology") Vol. 2" (supervised by Yo MIYATA, Kitaoji Shobo, 1997), page 14, the "P300 component" is generally a positive component of an event-related potential near a latency of 300 ms that is induced in response to a target stimulation in an oddball task.

Furthermore, it can be seen from FIG. 9 that, at the electrode positions C3, Cz, and C4, the lines jointed by black circles showing the zone average potential in the case of a high confidence of aural distinction and the lines jointed by white circles showing the zone average potential in the case of a low confidence of aural distinction differ in their potential distribution patterns (relative magnitudes). As a result of multiple comparison, a significant difference was found between the potential distribution patterns (p<0.05). This indicates that confidence of aural distinction can also be determined by using the potential distribution patterns at the electrode positions C3, Cz, and C4. Since the electrode positions C3, Cz, and C4 are positions at which the headband of overhead-type headphones would come in contact with the head, ease of electrode wearing is provided when headphones are used to make a speech sound intelligibility assessment.

The positive component at the electrode position Pz at a latency from 700 ms to 900 ms (FIG. 8) and the characteristic component at the electrode positions C3, C4, and Cz at a latency from 700 ms to 900 ms (FIG. 9) can be identified by various methods. For example, a method of applying threshold processing to the peak amplitude level near the latency of about 700 ms, a method of generating a template from a typical waveform of the aforementioned component and calculating a similarity level with that template, and the like can be used. Note that such a threshold value or template may be that of a typical user as prestored, or may be generated for each individual person.

In this experiment, each arithmetic mean was taken from about 40 summations of the data of six participants for each degree of confidence of aural distinction, this being in order to confirm the fact that a component which is characteristic to confidence of aural distinction is sure to appear in an event-related potential based on the point of audio presentation as a starting point. However, depending on the method of characteristic amount extraction (e.g., wavelet transformation of the waveform) or the method of identification (e.g., support vector machine learning), identification of a positive component is possible with no summations or only a small number of summations.

In the present specification, in order to define a component of an event-related potential, a point in time after the lapse of a predetermined time since a given point is expressed by referring to a "latency from 700 ms to 900 ms", for example. This means possible inclusion of a range from 700 ms to 900 ms around a specific point in time. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 300 ms±30 ms, 700 ms±50 ms).

Although the aforementioned "breadth of 30 ms to 50 ms" is a generic example of an individual difference in the P300 component, greater individual differences exist between users with respect to the aforementioned positive component at a latency from 700 ms to 900 ms, which is later in latency than P300. Therefore, the aforementioned positive component is preferably treated as having a broader breadth, e.g., a breadth of about 100 ms.

Thus, through the behavioral experiment and the electroencephalogram measurement experiment, the inventors have found that: (1) a speech sound intelligibility assessment is possible based on a user's confidence of aural distinction concerning audios; and (2) a positive component of an event-related potential at a latency from 700 ms to 900 ms based on the point of audio presentation as a starting point reflects the confidence of aural distinction. Therefore, with a method of estimating confidence of aural distinction concerning audios by using the positive component of an event-related potential as an index, a speech sound intelligibility assessment can be realized which requires no answer inputs. FIG. 10 shows correspondence between presence or absence of a positive component and confidence of aural distinction and ease of hearing, as compiled by the inventors. This correspondence diagram is created by taking the positive component at the electrode position Pz as an example.

Hereinafter, a speech sound intelligibility assessment system according to an embodiment of the present invention will be described. The speech sound intelligibility assessment system sequentially presents monosyllabic speech sounds in the form of audios, and makes an assessment of listening comprehension concerning speech sounds by utilizing presence or absence of a positive component in the event-related potential at a latency from 700 ms to 900 ms based on the point of audio presentation as a starting point. Such a speech sound intelligibility assessment system, which does not require answer inputs being made by the user, is unprecedentedly realized by the aforementioned two findings by the inventors.

3. Embodiment 1

Hereinafter, a first embodiment of a speech sound intelligibility assessment system which utilizes a positive component reflecting confidence of aural distinction will be described.

First, a speech sound intelligibility assessment system which sequentially presents audios, measures an event-related potential based on the point of each audio presentation as a starting point and detects a characteristic component to appear at a latency from 700 ms to 900 ms in the case of low confidence of aural distinction concerning audios, and evaluates listening comprehension of speech sounds will be described in outline. Thereafter, the construction and operation of a speech sound intelligibility assessment system including the speech sound intelligibility assessment apparatus will be described.

In the present embodiment, a probe electrode (which may also be referred to as a measurement electrode) is placed at the parietal position Pz, and a reference electrode is placed at the right or left mastoid, and an electroencephalogram was measured as a potential difference between the probe electrode and the reference electrode. As has been discussed with respect to the results of the electroencephalogram measurement experiment, it is also possible to determine confidence of aural distinction by mounting probe electrodes at the electrode positions Cz, C3, and C4, instead of Pz. The reference electrode may be anywhere in the ear periphery, e.g., at an earlobe or at a portion which comes in contact with an ear pad of a pair of headphones or eyeglasses.

Note that the level and polarity of the characteristic component of the event-related potential may vary depending on the position at which the electrode for electroencephalogram measurement is attached, and the manner in which the reference electrode and the probe electrode are set. However, based on the following description, those skilled in the art would be able to detect a characteristic component of the event-related potential and make a speech sound intelligibility assessment by making appropriate modifications depending on the specific reference electrode and probe electrode being set. Any such variant is encompassed within the present invention.

Note that, in the above description of the electroencephalogram measurement experiment, audios are experimentally presented to participants with normal hearing under three conditions of frequency gain attenuation, thus simulating the hearing of a person suffering from hypacusia. However, when making a speech sound intelligibility assessment for a person suffering from hypacusia, there is no particular need to present speech sounds that are difficult to aurally distinguish. In the present embodiment, it is assumed that speech sounds are presented whose gain for each frequency has been optimally adjusted based on a fitting method from audiograms of people suffering from hypacusia that were measured in advance.

3.1. Construction of Speech Sound Intelligibility Assessment System

FIG. 11 shows a construction and an environment of use for a speech sound intelligibility assessment system 100 according to the present embodiment. The speech sound intelligibility assessment system 100 is exemplified so as to correspond to a system construction of Embodiment 1 described later.

The speech sound intelligibility assessment system 100 includes a speech sound intelligibility assessment apparatus 1, an audio output section 11, and a biological signal measurement section 50. The biological signal measurement section 50 is connected to at least two electrodes A and B. Electrode A is attached at a mastoid of the user 5, whereas electrode B is attached at a position (so-called Pz) on the scalp of the user 5.

The speech sound intelligibility assessment system 100 presents a monosyllabic speech sound to the user 5 in the form of an audio, and determines the presence or absence of a positive component at a latency from 700 ms to 900 ms in an electroencephalogram (event-related potential) from the user 5 which is measured based on the point of audio presentation as a starting point. As used herein, a "latency from 700 ms to 900 ms" means a latency which is not less than 700 ms and not more than 900 ms, including the borders of 700 ms and 900 ms. Then, based on the presented audio and the presence or absence of a positive component, the speech sound intelligibility assessment system 100 automatically realizes a speech sound intelligibility assessment without answer inputs being made by the user 5.

An electroencephalogram from the user 5 is acquired by the biological signal measurement section 50 based on a potential difference between electrode A and electrode B. The biological signal measurement section 50 sends information corresponding to the potential difference to the speech sound intelligibility assessment apparatus 1 in a wireless or wired manner. FIG. 11 illustrates an example where the biological signal measurement section 50 wirelessly sends this information to the speech sound intelligibility assessment apparatus 1.

The speech sound intelligibility assessment apparatus 1 performs sound pressure control of the audio used for speech sound intelligibility assessment, controls presentation timing of the audio and the character, presents an audio via the audio output section 11 (e.g., loudspeakers) to the user 5.

FIG. 12 shows a hardware construction of the speech sound intelligibility assessment apparatus 1 according to the present embodiment. The speech sound intelligibility assessment apparatus 1 includes a CPU 30, a memory 31, and an audio controller 32. These elements are interconnected via a bus 34 so that data exchange among them is possible.

The CPU 30 executes a computer program 35 which is stored in the memory 31. A processing procedure as illustrated by a subsequently-described flowchart is described in the computer program 35. In accordance with the computer program 35, the speech sound intelligibility assessment apparatus 1 performs a process of controlling the entire speech sound intelligibility assessment system 100, by utilizing a speech sound database (DB) 71 which is also stored in the same memory 31. This process will be described in detail later.

In accordance with instructions from the CPU 30, the audio controller 32 generates an audio to be presented, and outputs the generated audio signal to the audio output section 11.

Note that the speech sound intelligibility assessment apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 12 (e.g., a PC) is able to function as the speech sound intelligibility assessment apparatus 1 according to the present embodiment. Note that the speech sound DB 71 does not need to be stored in the memory 31, but may be stored on a hard disk (not shown) which is connected to the bus 34.

FIG. 13 shows a functional block construction of the speech sound intelligibility assessment system 100 according to the present embodiment. The speech sound intelligibility assessment system 100 includes the audio output section 11, the biological signal measurement section 50, and the speech sound intelligibility assessment apparatus 1. FIG. 13 also shows detailed functional blocks of the speech sound intelligibility assessment apparatus 1. Specifically, the speech sound intelligibility assessment apparatus 1 includes a positive component detection section 60, a presented-speech sound control section 70, a speech sound DB 71, and a speech sound intelligibility assessment section 80. The user 5 block is illustrated for ease of explanation.

The respective functional blocks (except the speech sound DB 71) of the speech sound intelligibility assessment apparatus 1 correspond to functions which are realized by the CPU 30, the memory 31, and the audio controller 32 as a whole upon executing the program which has been described in conjunction with FIG. 12.

The speech sound DB 71 is a database of speech sounds for performing a speech sound intelligibility assessment. FIG. 14 shows an exemplary speech sound DB 71. In the speech sound DB 71 shown in FIG. 14, audio files to be presented, consonant labels, and grouped data based on likelihood of confusion (how likely confusion will occur) are associated. As for the stored audios, it is assumed that the gain for each frequency has been adjusted based on a fitting method from audiograms of people suffering from hypacusia that were measured in advance. The types of speech sounds to be stored may be speech sounds that are in the 57S list or the 67S list. The consonant labels are utilized when estimating a consonant that incurs a high probability of confusion by the user 5. The grouped data is utilized when estimating the group that incurs a high probability of confusion by the user 5. The grouping may be a rough category, a medium category, and a fine category, for example.

The rough category concerns categorization as to vowels, unvoiced consonants, and voiced consonants, which are respectively represented as 0, 1, and 2. The medium category defines sub-categorization among unvoiced consonants and among voiced consonants. The unvoiced consonants can be categorized into the sa-row (medium category: 1) and the ta-/ka-/ha-rows (medium category: 2), whereas the voiced consonants can be categorized into the ra-/ya-/wa-rows (medium category: 1) and the na-/ma-/ga-/za-/da-/ba-rows (medium category: 2). The fine category can be divided into the na-/ma-rows (fine category: 1) and the za-/ga-/da-/ba-rows (fine category: 2), for example. As for likelihood of confusion, the inventors relied on "HOCHOKI FITTINGU NO KANGAEKATA (or "Concept of Hearing Aid Fitting") (Kazuoki KODERA, Shindan To Chiryosha, 1999, p. 172).

FIG. 13 is again referred to. The presented-speech sound control section 70 determines a speech sound to be presented by referring to the speech sound DB 71. The presented-speech sound control section 70 may select and determine the speech sound by random order, or determine it by receiving information of speech sounds which are yet to be evaluated or to be evaluated again from the speech sound intelligibility assessment section 100, for example. Moreover, in order to obtain information as to which consonant or which speech sound group will incur a high probability of confusion, the presented-speech sound control section 70 may select an audio of a particular consonant or speech sound group.

The presented-speech sound control section 70 controls the audio output section 11 so as to present the speech sound thus determined to the user 5 in the form of an audio. Moreover, it sends a trigger and the actual audio to be presented to the positive component detection section 60, in accordance with the point of audio presentation.

The audio output section 11 reproduces and presents to the user 5 the monosyllabic audio which is designated by the presented-speech sound control section 70.

The biological signal measurement section 50, which is an electroencephalograph for measuring a biological signal of the user 5, measures an electroencephalogram as the biological signal. It is assumed that the user 5 has already put on the electroencephalograph. The electrode for electroencephalogram measurement is attached at the parietal Pz, for example.

The positive component detection section 60 receives the electroencephalogram of the user 5 measured by the biological signal measurement section 50. Then, based on the trigger received from the presented-speech sound control section 70 as a starting point, the positive component detection section 60 cuts out an event-related potential in a predetermined zone (e.g., a zone from −100 ms to 1000 ms) from the received electroencephalogram.

Thereafter, the positive component detection section 60 takes an arithmetic mean of the event-related potential which has been cut out, in accordance with the actual audio to be presented received from the presented-speech sound control section 70. The positive component detection section 60 may take an arithmetic mean by only selecting the same speech sound, or take an arithmetic mean by selecting speech sounds having the same consonant. An arithmetic mean may be taken for each of the rough category, the medium category, and the fine category of the grouping. Taking an arithmetic mean of only the same speech sound enables an assessment of aural distinction with respect to each speech sound. Taking an arithmetic mean of speech sounds having the same consonant enables an assessment as to which consonant induces a low intelligibility in aural distinction. Taking an arithmetic mean for each group enables an assessment of aural distinction as to the group, e.g., "between voiced consonants and unvoiced consonants, intelligibility in aural distinction is lower for the unvoiced consonants". The rough category, the medium category, and the fine category as mentioned herein refer to the categorizations which have been described with reference to FIG. 14.

By thus calculating an arithmetic mean, a speech sound-by-speech sound, consonant-by-constant, or group-by-group assessment of aural distinction is realized. From a consonantby-consonant or group-by-group arithmetic mean, a summed waveform is obtained with more than a few summations being made. Next, the positive component detection section 60 identifies an event-related potential, and determines the presence or absence of a positive component at a latency from 700 ms to 900 ms.

The positive component detection section 60 identifies the presence or absence of a positive component by the following method. For example, the positive component detection section 60 compares the maximum amplitude of a zone average potential at a latency from 700 ms to 900 ms or a latency from 700 ms to 900 ms against a predetermined threshold value. Then, if the zone average potential is greater than the threshold value, the case may be identified as "there is a positive component"; and if it is smaller, the case may be identified as "no positive component". Alternatively, the positive component detection section 60 may determine a similarity level (e.g., a correlation coefficient) between the waveform of an event-related potential at a latency from 700 ms to 900 ms and a predetermined template which is generated from the waveform of a typical positive component signal at a latency from 700 ms to 900 ms, and distinguish any similar case as "there is a positive component", and any dissimilar case as "no positive component". The predetermined threshold value or template may be calculated or generated from a prestored waveform of a positive component of a generic user, or calculated or generated from the waveform of a positive component of each individual person.

Note that a "positive component" would generally mean a voltage component of an event-related potential that is greater than 0 µV. However, in the context of the present specification, it is not a requirement for a "positive component" to be absolutely positive (i.e., greater than 0 µV). In the present specification, the presence or absence of a "positive component" is identified in order to identify a high or low confidence of aural distinction; therefore, so long as a significant highness or lowness of confidence of aural distinction is distinguishable, it does not matter if the zone average potential, etc., is 0 µV or less. For example, in FIG. 8, a zone of significant difference exists between about 700 ms and about 800 ms. In this zone, the event-related potential has a voltage value of about 0 µV. It is well expectable that a significant difference may exist even if the voltage value is about 0 µV throughout the zone of 800 ms±100 ms. Thus, it must be noted that it is not essential that a "positive component" be actually positive. In the present specification, any component of an event-related potential that is available for identifying highness or lowness of confidence of aural distinction may also be referred to as a "characteristic component". Even more broadly, it may also be referred to as a "component equal to or greater than a predetermined value" of an event-related potential.

From the positive component detection section 60, the speech sound intelligibility assessment section 80 receives information concerning the presence or absence of a positive component for each speech sound. Based on the received information, the speech sound intelligibility assessment section 100 evaluates speech sound intelligibility.

For example, the intelligibility assessment is made based on rules shown in FIG. 10 and the presence or absence of a positive component. As shown in FIG. 10, the speech sound intelligibility assessment section 80 evaluates the case of no positive component and a high confidence of aural distinction as "○" (=high intelligibility), and the case of some positive component and a low confidence of aural distinction as "Δ" (=low intelligibility).

FIGS. 15(*a*) to (*c*) show exemplary results of speech sound intelligibility assessment. FIGS. 15(*a*), (*b*), and (*c*) are examples of evaluating intelligibility on a speech sound-by-speech sound, consonant-by-constant, or group-by-group basis, by taking an arithmetic mean of each speech sound, each consonant, and each group, respectively. In the grouping of FIG. 15(*c*), the rough category concerns categorization as to vowels, unvoiced consonants, and voiced consonants, which are respectively represented as 0, 1, and 2; the medium category concerns sub-categorization of 1 and 2 among unvoiced consonants or among voiced consonants; and the fine category concerns categorization between the na-/ma-rows and the za-/ga-/da-/ba-rows, respectively represented as 1 and 2. Respectively, a ○/Δ evaluation can be made for each speech sound, each consonant, or each group. As a result, in the case of the speech sound " な (na)" in FIG. 15, which suffers a low speech sound intelligibility, it becomes clear whether: the intelligibility with respect to " な alone is low; intelligibility for the entire "na-row" is low; or the intelligibility is low for all "voiced consonants". Moreover, a potentially-low intelligibility can also be detected, as in the case of " や (ya)", for example, where " " や " is clearly aurally distinguishable but the intelligibility for the "ya-row" is still low. Moreover, a probability of "○" (which represents an "high speech sound intelligibility" assessment) may be calculated with respect to each speech sound, and the calculated probability of high intelligibility may be defined as the final speech sound intelligibility assessment.

3.2. Operation of Speech Sound Intelligibility Assessment System

Next, with reference to FIG. 16, an overall processing performed by the speech sound intelligibility assessment system 100 of FIG. 13 will be described. FIG. 16 is a flowchart showing a procedure of processing performed by the speech sound intelligibility assessment system 100.

At step S101, by referring to the speech sound DB 71, the presented-speech sound control section 70 determines a monosyllabic speech sound to be presented, and presents the speech sound to the user 5 in the form of an audio via the audio output section 11. Then, the presented-speech sound control section 70 sends the information of the presented audio and a trigger to the positive component detection section 60. The presented-speech sound control section 70 may randomly select from the speech sound DB 71 a speech sound to be presented, or exclusively select a speech sound of a particular consonant or a group.

At step S102, upon receiving the trigger from the presented-speech sound control section 70, the positive component detection section 60 cuts out an electroencephalogram from e.g. −100 ms to 1000 ms (i.e., an event-related potential) based on the trigger as a starting point, from the electroencephalogram measured by the biological signal measurement section 50. Then, an average potential from −100 ms to 0 ms is determined, and the baseline of the resultant event-related potential is corrected so that its average potential is 0 µV.

At step S103, based on the information of the speech sound to be presented which is received from the presented-speech sound control section 70, the positive component detection section 60 takes an arithmetic mean of the event-related potential cut out at step S102. The arithmetic mean may be taken for each speech sound, each consonant, or each group. Until a predetermined number of summations is attained, control returns to step S101 to repeat audio presentation. The "procedure of returning to step S101 from step S103" means repeating the process for another trial.

At step S104, the positive component detection section 60 identifies the waveform of the event-related potential whose arithmetic mean has been taken at step S103, and determines the presence or absence of a positive component at a latency from 700 ms to 900 ms. Identification of a positive component may be performed through comparison against a threshold value or comparison against a template, as mentioned above.

At step S105, receiving from the positive component detection section 60 the information of presence or absence of a positive component with respect to each speech sound, each consonant, or each group obtained at step S104, the speech sound intelligibility assessment section 100 makes a speech sound intelligibility assessment, and stores the result of assessment.

The criterion of speech sound intelligibility assessment is the presence or absence of a positive component as indicated in FIG. 10. Specifically, the speech sound intelligibility assessment section 100 evaluates the case of high intelligibility as "○" (=high intelligibility) and the case of low intelligibility as "Δ".

Through the above process, on the premise that a monosyllabic speech sound is presented in the form of an audio, it is possible to make a speech sound intelligibility assessment by using a positive component of an event-related potential at a latency from 700 ms to 900 ms based on the point of audio presentation as a starting point.

Note that, by implementing the speech sound intelligibility assessment apparatus 1 of the present embodiment in a portable size and weight, a speech sound intelligibility assessment can be realized in any acoustic environment in which the user will be using a hearing aid.

The present embodiment has been illustrated by assuming a speech sound intelligibility assessment for the Japanese language. However, any other language, e.g., English or Chinese, may be used so long as the speech sounds are monosyllabic. In the case of English, for example, monosyllabic words such as those shown in FIG. 17(a) may be presented, and an evaluation may be made on a word-by-word basis. Alternatively, an evaluation may be made on a phonetic symbol-by-phonetic symbol basis, as shown in FIG. 17(b). Moreover, words may be grouped based on probability of confusion as shown in FIG. 17(b), and a group-by-group assessment may be made.

In accordance with the speech sound intelligibility assessment system 100 of the present embodiment, a speech sound intelligibility assessment is realized as the user merely hears an audio and thinks of a corresponding hiragana, without answer inputs being made. As a result, the trouble of a hearing aid user in making a speech sound intelligibility assessment at a hearing aid shop is significantly reduced, for example.

Although FIG. 11 illustrates the audio output section 11 as loudspeakers, the audio output section 11 may be headphones. FIG. 18 shows the exterior appearance of headphones corresponding to the audio output section 11. Use of headphones, an enhanced mobility is provided, thus enabling a speech sound intelligibility assessment in an actual environment of use of the user.

Furthermore, as in the headphones of FIG. 18, an electroencephalograph corresponding to the biological signal measurement section 50 may also be incorporated together with electrodes. On a headband portion that is designed so as to extend in the neighborhood of parietal, an electrode Pz/Cz, which comes in contact with the position Pz or Cz, is provided. On ear cushions that are attached to the loudspeakers, a reference electrode and a ground electrode are provided. A electroencephalograph (not shown) may be provided inside the headphones, e.g., in the ear cushions or the headband portion. According to the present embodiment, upon wearing the headphones, the electrode Pz and the reference electrode/ground electrode will come into contact with the head and the ear peripheries, respectively, whereby an electroencephalogram measurement can be begun.

According to FIG. 9, when the electrode Cz is utilized, the polarity of Cz will be opposite to the polarity of the electrode Pz, i.e., negative when the confidence of aural distinction is low, and positive when the confidence of aural distinction is high. Therefore, a "positive component of the event-related potential" (or a "component equal to or greater than a predetermined value") in the above description should read as a "negative component of the event-related potential" (or a "component equal to or less than a predetermined value").

4. Embodiment 2

In the speech sound intelligibility assessment system 100 according to Embodiment 1, a speech sound intelligibility concerning audios which have previously been adjusted according to one type of fitting method and stored in the speech sound DB 71 is evaluated by examining the presence or absence of a characteristic component at a latency from 700 ms to 900 ms, such that this characteristic component reflects the confidence of aural distinction with respect to a presented audio.

The fitting theory-based approach is not quite accomplished yet, and several approaches are diversely present. The optimum fitting method differs from user to user. Therefore, making a speech sound intelligibility assessment by using a speech sound set that has been adjusted based on a plurality of types of fitting methods, instead of a speech sound set that has been adjusted based on one type of fitting method, will make it possible to obtain results that better suit each individual user.

Therefore, in the present embodiment, a speech sound intelligibility assessment system will be described which makes an assessment as to which fitting parameter is appropriate among a plurality of fitting parameters, and searches for a fitting method that is optimum for each user.

Fitting is realized by making a gain adjustment for each frequency, based on the relationship between the shape of an audiogram, a threshold value which is determined through a subjective report, a UCL (uncomfortable level: a sound loudness that is so loud that it is uncomfortable to a user) and MCL. According to page 79 of "HOCHOKI Q&A—YORIYOI FITTINGU NOTAMENI" (or "Hearing aids Q&A—For better fitting") (Zin KANZAKI et al., KANEHARA & Co., LTD., 2001), there are following types of fitting methods, for example: the half-gain method, in which an insertion gain of each frequency is made half of the threshold of hearing for that frequency; Berger's method, which, in addition to the above, slightly augments the gains from 1000 Hz to 4000 Hz by taking into consideration the frequency band and level of conversational voices; and the POGO method, which, based on the half-gain method, reduces the gains at 250 Hz and 500 Hz (where there is not so much speech sound information but a lot of noise component is included) by 10 dB and 5 dB, respectively; and the NAL-R method, which performs amplification so that a frequency of long-term sound analysis of words will fall around a comfortable level.

A speech sound intelligibility assessment system according to the present embodiment converts audio data stored in the speech sound DB 72 by using several fitting methods, as is done by an actual hearing aid, presents a plurality of kinds of converted audios to a user, and makes an assessment as to which fitting method is the best by utilizing a characteristic component which is induced in connection with confidence of aural distinction based on the point of audio presentation as a starting point. Conversion into the plurality of kinds of audios is realized by adjusting the sound level for each frequency. For example, in the case where the half-gain method is used as the fitting method, the gain of each frequency is adjusted to be a half of the threshold of hearing, based on an audiogram of the user.

FIG. 19 shows a functional block construction of a speech sound intelligibility assessment system 200 according to the present embodiment. The speech sound intelligibility assessment system 200 includes the audio output section 11, the biological signal measurement section 50, and a speech sound intelligibility assessment apparatus 2. Any block which has an identical counterpart in FIG. 13 is denoted by a like reference numeral, and the description thereof is omitted. The hardware construction of the speech sound intelligibility assessment apparatus 2 is as shown in FIG. 12. The speech sound intelligibility assessment apparatus 2 of the present embodiment shown in FIG. 19 is realized as a program which defines a different process from that of the program 35 described in Embodiment 1 (FIG. 12) is executed.

In order to describe a method of determining confidence of aural distinction based on an electroencephalogram measured at Cz, C3, and C4, it is assumed in the present embodiment that probe electrodes are disposed at Cz, C3, and C4, for example, and a reference electrode is disposed at the right or left mastoid. However, as described in Embodiment 1, a probe electrode may be disposed at Pz, and a reference electrode may be disposed in an ear periphery.

The speech sound intelligibility assessment apparatus 2 of the present embodiment differs from the speech sound intelligibility assessment apparatus 1 of Embodiment 1 in that an aural distinction confidence determination section 61 is provided instead of the positive component detection section 60; a speech sound DB 72 is provided instead of the speech sound DB 71; and a fitting method switching section 90 and a fitting method evaluation section 91 are provided instead of the speech sound intelligibility assessment section 80.

Hereinafter, the aural distinction confidence determination section 61, the speech sound DB 72, the fitting method switching section 90, and the fitting method evaluation section 91 will be described.

The first difference, i.e., the aural distinction confidence determination section 61 acquires an electroencephalogram from an electrode(s) which is disposed on the headband position of headphones. Then, the aural distinction confidence determination section 61 cuts out an event-related potential from the electroencephalogram based on the point of audio presentation as a starting point, takes an arithmetic mean thereof, and determines confidence of aural distinction by detecting a characteristic component which is induced in the case of a low confidence of aural distinction. The method of cutting out a waveform and the method of taking an arithmetic mean are similar to those of the positive component detection section 60 in the speech sound intelligibility assessment system 100.

A characteristic component is detected in the following manner, for example. In the case where the measurement electrode is at Cz, the aural distinction confidence determination section 61 compares a zone average potential at a latency from 700 ms to 900 ms against a predetermined threshold value. Then, the aural distinction confidence determination section 61 identifies the case where the zone average potential is greater than the threshold value as "there is no characteristic component", and the case where the zone average potential is smaller than the threshold value as "there is some characteristic component". The "predetermined threshold value" may be calculated from a prestored waveform of a characteristic component of a generic user in the case of low confidence of aural distinction, or calculated from the waveform of the characteristic component of each individual person.

Now, another example of a method of characteristic component detection will be described. In the case where measurement electrodes are at C3, Cz, and C4, based on the results shown in FIG. 9, the aural distinction confidence determination section 61 may calculate a zone average potential of event-related potentials at a latency from 700 ms to 900 ms which are acquired by using the electrodes C3, Cz, and C4, and detect a characteristic component based on the relative magnitudes of the zone average potentials. For example, the aural distinction confidence determination section 61 may identify the case where the zone average potential of the electrodes C3 and C4 is greater than that of the electrode Cz as "there is some characteristic component", and the case where the zone average potential of the electrodes C3 and C4 is smaller than that of the electrode Cz as "there is no characteristic component". Thus, erroneous detections are reduced by performing a determination based on the relative magnitudes of zone average potentials of a plurality of electrodes.

The second difference from the Embodiment 1, i.e., the speech sound DB 72, is a database of speech sounds for selecting an optimum fitting method. FIG. 20 shows an example of the speech sound DB 72. The difference between the speech sound DB 72 and the speech sound DB 71 shown in FIG. 14 is that the speech sound DB 72 retains a plurality of audio sets obtained by adjusting results of audiogram measurements of users based on a plurality of fitting methods. The audio sets 72a, 72b, and 72c are adjusted based on fitting methods A, B, and C, respectively. In each audio set, the frequency gain of the speech sounds is adjusted according to a fitting method.

Similarly to the speech sound DB 71 shown in FIG. 14, the items in each fitting method in the speech sound DB shown in FIG. 20 are audio files to be presented, consonant labels, and grouped data based on likeliness of confusion (how likely confusion will occur). The types of speech sounds to be stored may be speech sounds that are in the 57S list or the 67S list. The consonant labels are utilized when estimating a consonant that incurs a high probability of confusion by the user 5. The grouped data is utilized when estimating the group that incurs a high probability of confusion by the user 5. The grouping may be a rough category, a medium category, and a fine category, similarly to the speech sound DB 71, for example.

Although FIG. 20 is only directed to the Japanese language, speech sounds of any other language besides Japanese, e.g., English or Chinese, may be used so long as the speech sounds are monosyllabic. In the case of English, for example, audios that are obtained by adjusting the monosyllabic words exemplified in FIG. 17(a) by a plurality of fitting methods may be stored in the database.

The third difference from Embodiment 1, i.e., the fitting method switching section 90, selects a fitting method by regular or random order with reference to the speech sound DB 72, and acquires an audio of a speech sound whose respective frequency gains are adjusted by the selected fitting method. As mentioned above, possible fitting methods include the half-gain method, the Berger method, the POGO method, the NAL-R method, and the like. Note that "selecting a fitting method" is synonymous to selecting one of the plurality of audio sets stored in the speech sound DB 72. The audios of the speech sounds within the acquired audio set are presented to the user 5 via the audio output section 11.

The fitting method evaluation section 91 receives from the aural distinction confidence determination section 61 the information of a zone average potential at a latency from e.g. 700 ms to 900 ms as the amplitude of an event-related potential based on the point of audio presentation as a starting point, and receives from the fitting method switching section 90 the information of the fitting method for the presented audio.

Then, with respect to each fitting method, the fitting method evaluation section 91 determines the presence or absence of a positive component for each speech sound, each consonant, or each speech sound group, for example.

FIG. 21 shows examples of results of speech sound intelligibility assessment for different speech sounds according to fitting methods A to C. For example, fitting method A is the half-gain method, fitting method B is Berger's method, and fitting method C is the POGO method.

Next, the fitting method evaluation section 91 compares the respective speech sound intelligibility assessment results of the fitting methods. A "speech sound intelligibility assessment result" is a result of determination as to whether the user 5 has aurally comprehended a presented speech sound or not, i.e., whether the speech sound intelligibility is high or not. For example, the fitting methods can be ordered in terms of their relative optimumness by comparing their respective probabilities that the result of speech sound intelligibility assessment is "○" (=intelligibility is high).

FIG. 22 shows exemplary assessment results of fitting methods. These assessment results are calculated based on the examples of FIG. 21. FIG. 22 illustrates an example where, based on the probability of speech sounds with high speech sound intelligibility, fitting method A having a high probability is evaluated as "⊚" i.e., the fitting method that is the most suitable to the user 5, and fitting method B having a low probability is evaluated as "X", i.e., not suitable to the user 5. Fitting method C, whose assessment result is the second best, is indicated as "Δ".

Although an "⊚", "X" or "Δ" evaluation is given to each fitting method in accordance with its probability of speech sounds with high speech sound intelligibility in the aforementioned process (FIG. 22), this is only an example. So long as an optimum fitting method can be selected, there is no limitation as to how the ratings of the fitting methods are indicated. Moreover, a threshold value for the probability may be previously defined, and any fitting method that exceeds this threshold value may be indicated to the user of the hearing aid as appropriate.

Next, with reference to the flowchart of FIG. 23, an overall procedure of processing that is performed in the speech sound intelligibility assessment system 200 will be described.

FIG. 23 shows a processing procedure by the speech sound intelligibility system 200 of the present embodiment. In FIG. 23, any step where a process identical to a process by the speech sound intelligibility assessment system 100 (FIG. 16) will be denoted by a like reference numeral, and the description thereof will be omitted.

The processes by the speech sound intelligibility assessment system 200 of the present embodiment differ from the processes of the speech sound intelligibility assessment system 200 of Embodiment 1 in that step S104 of determining the presence or absence of a positive component at a latency from 700 ms to 900 ms based on the point of audio presentation as a starting point and step S105 of speech sound intelligibility assessment are omitted, and that step S201 to step S204 of performing a fitting method evaluation are newly introduced.

At step S201, by referring to the speech sound DB and an audiogram of the user 5 which was previously measured, the fitting method switching section 90 selects an audio set to be subjected to speech sound intelligibility assessment from among a plurality of audio sets that have been adjusted by a plurality of fitting methods.

At step S202, the aural distinction confidence determination section 61 detects the presence or absence of a characteristic component which is induced in the case of a low confidence of aural distinction, and determines a degree of confidence of aural distinction based on the result of detection.

For example, if the only measurement electrode is at Cz in the central portion, the zone average potential at a latency from 700 ms to 900 ms is compared against a predetermined threshold value, and the case where it is greater than the threshold value is identified as "there is no characteristic component", and the case where it is smaller is identified as "there is some characteristic component". Alternatively, if the measurement electrodes are at C3, Cz, and C4, for example, a zone average potential at a latency from 700 ms to 900 ms is calculated for each of C3, Cz, and C4, and based on the relative magnitudes of the zone average potentials at the respective positions, the case where C3 and C4 are greater than Cz in zone average potential is identified as "there is some characteristic component", and the case where they are smaller is identified as "there is no characteristic component".

At step S203, based on the information of confidence of aural distinction received from the aural distinction confidence determination section 61, the fitting method evaluation section 91 calculates a probability of speech sounds with high confidence for each fitting method.

At step S204, based on the probability of clear speech sounds calculated at step S203, the fitting method evaluation section 91 indicates the fitting method that has the greatest probability to the hearing aid user as an optimum fitting method.

Through such processes, a probability of clear speech sounds is measured with respect to each type of fitting method, and for each speech sound, each consonant, or each speech sound group of each fitting method, thus making it possible to find a fitting method that is optimum to the user through probability comparison. Thus, evaluations of fitting methods can be made.

Since the speech sound intelligibility assessment apparatus 2 of the present embodiment is portable, a speech sound intelligibility assessment can be realized in any acoustic environment in which the user will be using a hearing aid.

In accordance with the speech sound intelligibility assessment system 200 of the present embodiment, it is possible to easily and automatically ascertain an optimum fitting method for each user, with respect to speech sounds that are actually output from a hearing aid. This eliminates the need for any fitting to be made for searching purposes, and thus significantly reduces the amount of time required for fitting.

In the description of the above Embodiments, it is assumed that the electrode position(s) is at Cz, etc., according to the International 10-20 system, for example. However, it is difficult to identify an exact electrode position on the head of each user that corresponds to the Cz position. Therefore, the electrode position may be a position that is fairly deemed as Cz (position in the neighborhood of Cz). The same is also true of Pz and other electrode positions.

A speech sound intelligibility assessment apparatus according to the present invention and a speech sound intelligibility assessment system incorporating the speech sound intelligibility assessment apparatus can automatically make an assessment of speech sound intelligibility, and can be used for the fitting of a hearing aid by all kinds of people, including users who cannot answer with speech or button pressing, e.g., physically handicapped users and infants.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A speech sound intelligibility assessment system, comprising:
   a biological signal measurement section for measuring an electroencephalogram signal of a user;
   a presented-speech sound control section for determining a speech sound to be presented by referring to a speech sound database retaining a plurality of monosyllabic speech sounds;
   an audio output section for presenting the speech sound determined by the presented-speech sound control section as an audio;
   a characteristic component detection section for utilizing the electroencephalogram signal of the user measured by the biological signal measurement section, determining presence or absence of a characteristic component of an event-related potential at 800 ms±100 ms from a point of presenting the audio; and
   a speech sound intelligibility assessment section for, based on a result of determination by the characteristic component detection section, determining whether the user has aurally comprehended the speech sound or not.

2. The speech sound intelligibility assessment system of claim 1, wherein,
   the event-related potential is acquired by utilizing an electrode position Pz according to the International 10-20 system, and the characteristic component detection section determines that a characteristic component exists in the event-related potential when a component equal to or greater than a predetermined value is present in the event-related potential; and
   if the characteristic component detection section determines that the characteristic component does not exist in the event-related potential, the speech sound intelligibility assessment section determines that the user has aurally comprehended the speech sound, and
   if the characteristic component detection section determines that the characteristic component exists in the event-related potential, the speech sound intelligibility assessment section determines that the user has not aurally comprehended the speech sound.

3. The speech sound intelligibility assessment system of claim 1, wherein,
   the event-related potential is acquired by utilizing an electrode position Cz according to the International 10-20 system, and the characteristic component detection section determines that a characteristic component is present in the event-related potential when a component equal to or less than a predetermined value is present in the event-related potential; and
   if the characteristic component detection section determines that the characteristic component does not exist in the event-related potential, the speech sound intelligibility assessment section determines that the user has aurally comprehended the speech sound, and
   if the characteristic component detection section determines that the characteristic component exists in the event-related potential, the speech sound intelligibility assessment section determines that the user has not aurally comprehended the speech sound.

4. The speech sound intelligibility assessment system of claim 1, wherein, in the speech sound database, an audio, consonant information, and a group concerning probability of confusion are associated with each of a plurality of speech sounds.

5. The speech sound intelligibility assessment system of claim 4, wherein the speech sound intelligibility assessment section evaluates a speech sound intelligibility for each speech sound, each consonant, or each group concerning probability of confusion.

6. The speech sound intelligibility assessment system of claim 1, wherein,
   the speech sound database retains a plurality of audio sets whose frequency gain is adjusted by a plurality of fitting methods; and
   the speech sound intelligibility assessment system further comprises a fitting method switching section for selecting one of the plurality of fitting methods by regularly or randomly switching between the audio sets retained in the speech sound database.

7. The speech sound intelligibility assessment system of claim 6, wherein,
   when the audio output section presents as an audio a speech sound from within an audio set selected by the fitting method switching section,
   among the plurality of fitting methods, the speech sound intelligibility assessment section makes a comparison as to the respective results of determination as to whether the speech sound has been aurally comprehended or not, and determines the fitting method having a highest probability that the speech sound has been aurally comprehended to be suitable to the user.

8. A speech sound intelligibility assessment system comprising:
   a presented-speech sound control section for determining a speech sound to be presented by referring to a speech sound database retaining a plurality of monosyllabic speech sounds;
   an audio output section for presenting the speech sound determined by the presented-speech sound control section as an audio;
   a characteristic component detection section for utilizing an electroencephalogram signal of a user measured by a biological signal measurement section for measuring the electroencephalogram signal of the user to determine presence or absence of a characteristic component of an event-related potential at 800 ms±100 ms from a point of presenting the audio; and
   a speech sound intelligibility assessment section for, based on a result of determination by the characteristic component detection section, determining whether the user has aurally comprehended the speech sound or not.

9. A speech sound intelligibility assessment method carried out by a speech sound intelligibility assessment system having a biological signal measurement section, a presented-speech sound control section, an audio output section, a characteristic component detection section, and a speech sound intelligibility assessment section,
   the speech sound intelligibility assessment method comprising the steps of:

measuring an electroencephalogram signal of a user with the biological signal measurement section;

determining a speech sound to be presented with the presented-speech sound control section by referring to a speech sound database retaining a plurality of monosyllabic speech sounds;

presenting the determined speech sound as an audio with the audio output section;

from the measured electroencephalogram signal of the user, determining with the characteristic component detection section a presence or absence of a characteristic component of an event-related potential at 800 ms±100 ms from a point of presenting the audio; and determining with the speech sound intelligibility assessment section whether the user has aurally comprehended the speech sound or not based on a result of determination by the characteristic component detection section.

10. A non-transitory computer-readable medium having a computer program stored thereon, wherein the computer program causes a computer to execute the steps of:

receiving a measured electroencephalogram signal of a user;

determining a speech sound to be presented by referring to a speech sound database retaining a plurality of monosyllabic speech sounds;

presenting the determined speech sound as an audio;

from the measured electroencephalogram signal of the user, determining presence or absence of a characteristic component of an event-related potential at 800 ms±100 ms from a point of presenting the audio; and determining whether the user has aurally comprehended the speech sound or not based on a result of the determination of presence or absence of a characteristic component.

* * * * *